(12) United States Patent
Ali et al.

(10) Patent No.: US 11,690,845 B2
(45) Date of Patent: Jul. 4, 2023

(54) METHODS OF ADMINISTERING ELAGOLIX

(71) Applicant: AbbVie Inc., North Chicago, IL (US)

(72) Inventors: Farah N. Ali, Wilmette, IL (US); Nael M. Mostafa, Libertyville, IL (US); Ahmed Nader, Libertyville, IL (US); Mohamad Shebley, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 17/004,817

(22) Filed: Aug. 27, 2020

(65) Prior Publication Data

US 2021/0275527 A1    Sep. 9, 2021

Related U.S. Application Data

(60) Provisional application No. 63/022,684, filed on May 11, 2020, provisional application No. 62/985,560, filed on Mar. 5, 2020.

(51) Int. Cl.
| | | |
|---|---|---|
| *A61K 31/513* | (2006.01) | |
| *A61K 31/137* | (2006.01) | |
| *A61K 9/00* | (2006.01) | |
| *A61K 31/57* | (2006.01) | |

(Continued)

(52) U.S. Cl.
CPC .......... *A61K 31/513* (2013.01); *A61K 9/0053* (2013.01); *A61K 31/137* (2013.01); *A61K 31/4439* (2013.01); *A61K 31/565* (2013.01); *A61K 31/57* (2013.01)

(58) Field of Classification Search
CPC .. A61K 31/513; A61K 9/0053; A61K 31/137; A61K 31/4439; A61K 31/565; A61K 31/57
See application file for complete search history.

(56) References Cited

U.S. PATENT DOCUMENTS

| | | |
|---|---|---|
| 9,949,974 B2 | 4/2018 | Goss et al. |
| 10,537,572 B2 | 1/2020 | Goss et al. |
| 10,682,351 B2 | 6/2020 | Goss et al. |

(Continued)

FOREIGN PATENT DOCUMENTS

| | | | |
|---|---|---|---|
| WO | 2014143669 A1 | 9/2014 | |
| WO | WO-2014143669 A1 * | 9/2014 | ........... A61K 31/513 |

(Continued)

OTHER PUBLICATIONS

Archer, D.F., et al., "Elagolix for the management of heavy menstrual bleeding associated with uterine fibroids: results from a phase 2a proof-of-concept study," Fertil Steril. 2017, vol. 108(1), pp. 152-160.

(Continued)

*Primary Examiner* — San Ming R Hui
(74) *Attorney, Agent, or Firm* — Neal, Gerber & Eisenberg LLP

(57) ABSTRACT

The present disclosure relates to the use of GnRH receptor antagonists for the treatment of endometriosis, uterine fibroids, polycystic ovary syndrome (PCOS), or adenomyosis. In particular, the present disclosure describes methods for treating such gynecological disorders, where the methods involve administration of elagolix and may further involve co-administration of a CYP2B6 substrate (e.g., bupropion) or a CYP2C19 substrate (e.g., omeprazole).

17 Claims, 6 Drawing Sheets

| N | Period 1 | | Period 2 | |
|---|---|---|---|---|
| | Day 1 | Days 1-10 | Day 11 | Days 12-14 |
| 24 adult female subjects | 150 mg Oral Bupropion | 5 Days Washout | Elagolix 300 mg BID / 150 mg Oral Bupropion | Elagolix 300 mg BID |

| Intensive PK Sampling | Day 1, Period 1 (Bupropion) | Day 11, Period 2 (Bupropion + Elagolix) |
|---|---|---|

Effect of Elagolix on single dose Bupropion ⟶ Period 2, Day 11 vs. Period 1, Day 1

(51) Int. Cl.
*A61K 31/565* (2006.01)
*A61K 31/4439* (2006.01)

(56) References Cited

U.S. PATENT DOCUMENTS

| | | | |
|---|---|---|---|
| 10,881,659 | B2 | 1/2021 | Chwalisz et al. |
| 11,045,470 | B2 | 6/2021 | Chwalisz et al. |
| 11,344,551 | B2 | 5/2022 | Chwalisz et al. |
| 2007/0191403 | A1 | 8/2007 | Guo et al. |
| 2011/0312925 | A1 | 12/2011 | Labrie |
| 2019/0209562 | A1 | 7/2019 | Chwalisz et al. |
| 2020/0163965 | A1 | 5/2020 | Chwalisz et al. |
| 2020/0268752 | A1 | 8/2020 | Goss et al. |
| 2021/0154207 | A1 | 5/2021 | Chwalisz et al. |
| 2021/0254056 | A1 | 8/2021 | Liu et al. |
| 2021/0275528 | A1 | 9/2021 | Chwalisz et al. |
| 2021/0308135 | A1 | 10/2021 | Shebley |

FOREIGN PATENT DOCUMENTS

| | | | |
|---|---|---|---|
| WO | 2017040841 | A1 | 3/2017 |
| WO | 2018204764 | A1 | 11/2018 |

OTHER PUBLICATIONS

Carr, B., et al., "Elagolix, an oral GnRH antagonist for endometriosis-associated pain: a randomized controlled study," Journal of Endometriosis and Pelvic Pain Disorders, 2013, vol. 5 (3), pp. 105-115.

Carr B., et al., "Elagolix, an Oral GnRH Antagonist, Versus Subcutaneous Depot Medroxyprogesterone Acetate for the Treatment of Endometriosis: Effects on Bone Mineral Density," Reproductive sciences, 2014, vol. 21 (11), pp. 1341-1351.

Chen C., et al., "Discovery of Sodium R-(+)-4-{2-[5-(2-Fluoro-3-methoxyphenyl)-3-{2-fluoro-6-[trifluoromethyl]benzyl)-4-methyl-2,6-dioxo-3,6-dihydro-2Hpyrimidin-1-yl]-1-phenylethylamino}butyrat e (Elagolix), a Potent and Orally Available Nonpeptide Antagonist of the Human Gonadotropin-Releasing Hormone Receptor," Journal Of Medicinal Chemistry, American Chemical Society, US, 2008, vol. 51 (23), pp. 7478-7485.

Diamond M.P., et al., "Elagolix Treatment for Endometriosis-Associated Pain: results from a Phase 2, Randomized , Double-Blind, Placebo-Controlled Study", Reproductive Sciences, Sage Publications, Inc, US, 2014, vol. 21 (3), pp. 363-371.

Kim, S., et al., "Discovery of an Orally Bioavailable Gonadotropin-Releasing Hormone Receptor Antagonist," J Med Chem, 2016, vol. 59(19), pp. 9150-9172.

Ng, J., et al., "Dose-Dependent Suppression of Gonadotropins and Ovarian Hormones by Elagolix in Healthy Premenopausal Women," J Clin Endocrinol Metab., 2017, vol. 102(5), pp. 1683-1691.

Struthers R.S. et al., "Suppression of Gonadotropins and Estradiol in Premenopausal Women by Oral Administration of the Nonpeptide Gonadotropin-Releasing Hormone Antagonist Elagolix," The Journal of Clinical Endocrinology & Metabolism, 2009, vol. 94 (2), pp. 545-551.

Taylor H.S., et al., "Treatment of Endometriosis-Associated Pain with Elagolix, an Oral GnRH Antagonist," The New England Journal of Medicine, 2017, vol. 377, pp. 28-40.

AbbVie Inc., Prescribing Information for ORILISSA (elagolix), revised Jul. 2018, 34 pages.

AbbVie Inc., Prescribing Information for ORILISSA (elagolix), revised Aug. 2019, 30 pages.

AbbVie Inc., Prescribing Information for ORIAHHN (elagolix, estradiol, and norethindrone acetate capsules; elagolix capsules), revised May 2020, 32 pages.

Anonymous, Drugs@FDA: FDA-Approved Drugs entry for ORILISSA (elagolix sodium), available at https://www.accessdata.fda.gov [retrieved on Feb. 25, 2022], 2 pages.

Gassman, Audrey, Letter regarding supplemental new drug application, Nda 210450/S-002, dated Aug. 28, 2019, 4 pages.

International Search Report and Written Opinion for Application No. PCT/US2020/048181, dated Nov. 2, 2020, 11 pages.

* cited by examiner

FIG. 1

| N | Period 1 | | | Period 2 | |
|---|---|---|---|---|---|
| | Day 1 | | Days 1-10 | Day 11 | Days 12-14 |
| 24 adult female subjects | 150 mg Oral Bupropion | 5 Days Washout | Elagolix 100 mg BID | Elagolix 200 mg BID / 150 mg Oral Bupropion | Elagolix 100 mg BID |
| Intensive PK Sampling ⟶ | Day 1, Period 1 (Bupropion) | | | Day 11, Period 2 (Bupropion + Elagolix) | |
| Effect of Elagolix on single dose Bupropion ⟶ | | | | Period 2, Day 11 vs. Period 1, Day 1 | |

METHODS OF ADMINISTERING ELAGOLIX

RELATED APPLICATION

This application claims the benefit of U.S. Provisional Application No. 62/985,560, filed Mar. 5, 2020 and U.S. Provisional Application No. 63/022,684, filed May 11, 2020. The contents of each application are incorporated herein by reference.

TECHNICAL FIELD

The present disclosure pertains to the use of GnRH receptor antagonists in the treatment of subjects suffering from, for example, endometriosis, uterine fibroids, polycystic ovary syndrome (PCOS), or adenomyosis.

BACKGROUND

An orally-administered, nonpeptide small molecule competitive GnRH receptor antagonist, elagolix, has recently been approved for the management of moderate to severe pain associated with endometriosis. Elagolix is currently in development for the management of heavy menstrual bleeding associated with uterine fibroids.

Bupropion is an antidepressant of the aminoketone class that may be used for the treatment of major depressive disorder (MDD), for the prevention of seasonal affective disorder (SAD), and as an aid for smoking cessation treatment. Bupropion is primarily metabolized to hydroxybupropion by CYP2B6. Therefore, the potential exists for drug interactions between bupropion and drugs that are inhibitors or inducers of CYP2B6.

There are reports of evidence implicating a relationship between peak plasma concentrations of bupropion and some adverse events. See Fava, et al., Prim Care Companion J Clin Psychiatry 7(3): 106-113, 2005.

Omeprazole, a substituted benzimidazole, is a proton pump inhibitor that inhibits gastric acid secretion. Omeprazole is metabolized via multiple pathways with CYP2C19-mediated formation of 5-hydroxyomeprazole and CYP3A-mediated formation of omeprazole sulfone being the main pathways responsible for omeprazole elimination. Therefore, the potential exists for drug interactions between omeprazole and drugs that are inhibitors or inducers of CYP2C19 and/or CYP3A.

SUMMARY OF THE INVENTION

In one aspect, this disclosure provides a method for treating a gynecological disorder in a patient in need thereof. The method comprises orally administering to the patient sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino) butanoate ("elagolix sodium"), wherein the patient concomitantly receives treatment with a CYP2B6 substrate. In certain embodiments, the CYP2B6 substrate is bupropion.

In certain embodiments, elagolix sodium is orally administered to the patient according to a recommended elagolix dosing schedule. In some such embodiments, the recommended elagolix dosing schedule comprises twice daily oral administration of elagolix sodium in an amount equivalent to 300 mg of elagolix free acid to achieve a total daily dose equivalent to 600 mg of elagolix free acid. In certain embodiments, concomitant administration of the CYP2B6 substrate and elagolix sodium according to the recommended elagolix dosing schedule results in an altered CYP2B6 substrate pharmacokinetic parameter relative to the CYP2B6 substrate pharmacokinetic parameter as obtained for administration of the CYP2B6 substrate alone. For example, concomitant administration of a CYP2B6 substrate and elagolix sodium according to a recommended elagolix dosing schedule may result in an increased $C_{max}$ for the CYP2B6 substrate and/or a metabolite thereof relative to the $C_{max}$ for the CYP2B6 substrate and/or a metabolite thereof obtained following administration of bupropion alone. In a particular example, concomitant administration of bupropion and elagolix sodium according to a recommended elagolix dosing schedule may result in an increased bupropion $C_{max}$ and/or an increased hydroxybupropion $C_{max}$ relative to the bupropion $C_{max}$ and/or hydroxybupropion $C_{max}$, respectively, obtained following administration of bupropion alone.

In certain embodiments, the CYP2B6 substrate is administered to the patient according to a recommended CYP2B6 substrate dosing schedule. In certain embodiments, the CYP2B6 substrate is administered to the patient according to a modified CYP2B6 substrate dosing schedule. The modified CYP2B6 substrate dosing schedule may comprise less frequent administration of the CYP2B6 substrate and/or a lower total daily dose relative to the recommended CYP2B6 substrate dosing schedule. For example, according to a modified CYP2B6 substrate dosing schedule, the CYP2B6 substrate may be administered to the patient at a reduced CYP2B6 substrate dosing frequency. In some such embodiments, the CYP2B6 substrate is bupropion and the reduced CYP2B6 dosing frequency is once per day; or, alternatively once or twice every other day. As another example, according to a modified CYP2B6 substrate dosing schedule, the CYP2B6 substrate may be administered to the patient to at a reduced CYP2B6 substrate total daily dose. In some such embodiments, the CYP2B6 substrate is bupropion and the reduced CYP2B6 substrate total daily dose is less than 450 mg per day; alternatively, less than 400 mg per day; alternatively, less than 300 mg per day; alternatively, less than 200 mg per day; or alternatively, less than 100 mg per day.

In one aspect, this disclosure provides a method for treating a gynecological disorder in a patient in need thereof. The method comprises orally administering to the patient sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino) butanoate ("elagolix sodium"), wherein elagolix sodium is administered in an amount equivalent to 300 mg of elagolix free acid twice daily; wherein the patient receives a once daily dose of 150 mg of bupropion; and wherein:

(i) a ratio of $C_{max}$ for bupropion following co-administration of bupropion with elagolix to $C_{max}$ for bupropion following administration of bupropion alone is between about 1.104 and about 1.407, such as about 1.246;

(ii) a ratio of $AUC_{inf}$ for bupropion following co-administration of bupropion with elagolix to $AUC_{inf}$ for bupropion following administration of bupropion alone is between about 0.910 and about 1.023, such as about 0.965;

(iii) a ratio of $C_{max}$ for hydroxybupropion following co-administration of bupropion with elagolix to $C_{max}$ for hydroxybupropion following administration of bupropion alone is between about 1.216 and about 1.427, such as about 1.317; and/or (iv) a ratio of $AUC_{inf}$ for hydroxybupropion following co-administration of bupropion with elagolix to $AUC_{inf}$ for hydroxybupropion following administration of bupropion alone is between about 0.993 and about 1.137, such as about 1.063.

In one aspect, this disclosure provides a method for treating a gynecological disorder in a patient in need thereof. The method comprises orally administering to the patient sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate ("elagolix sodium"), wherein the patient concomitantly receives treatment with a CYP2C19 substrate. In certain embodiments, the CYP2C19 substrate is omeprazole.

In certain embodiments, elagolix sodium is orally administered to the patient according to a recommended elagolix dosing schedule. In some such embodiments, the recommended elagolix dosing schedule comprises twice daily oral administration of elagolix sodium in an amount equivalent to 300 mg of elagolix free acid to achieve a total daily dose equivalent to 600 mg of elagolix free acid. In certain embodiments, concomitant administration of the CYP2C19 substrate and elagolix sodium according to the recommended elagolix dosing schedule results in an altered CYP2C19 substrate pharmacokinetic parameter relative to the CYP2C19 substrate pharmacokinetic parameter as obtained for administration of the CYP2C19 substrate alone. For example, concomitant administration of a CYP2C19 substrate and elagolix sodium according to a recommended elagolix dosing schedule may result in an increased $C_{max}$ and/or $AUC_{inf}$ for the CYP2C19 substrate and/or a metabolite thereof relative to the $C_{max}$ and/or $AUC_{inf}$ for the CYP2C19 substrate and/or a metabolite thereof obtained following administration of omeprazole alone. In a particular example, concomitant administration of omeprazole and elagolix sodium according to a recommended elagolix dosing schedule may result in an increased omeprazole $C_{max}$ and/or an increased omeprazole sulfone $C_{max}$ relative to the omeprazole $C_{max}$ and/or omeprazole sulfone $C_{max}$, respectively, obtained following administration of omeprazole alone. In another particular example, concomitant administration of omeprazole and elagolix sodium according to a recommended elagolix dosing schedule may result in an increased omeprazole $AUC_{inf}$ and/or an increased omeprazole sulfone $AUC_{inf}$ relative to the omeprazole $AUC_{inf}$ and/or omeprazole sulfone $AUC_{inf}$, respectively, obtained following administration of omeprazole alone In certain embodiments, the CYP2C19 substrate is administered to the patient according to a recommended CYP2C19 substrate dosing schedule. In certain embodiments, the CYP2C19 substrate is administered to the patient according to a modified CYP2C19 substrate dosing schedule. The modified CYP2C19 substrate dosing schedule may comprise less frequent administration of the CYP2C19 substrate and/or a lower total daily dose relative to the recommended CYP2C19 substrate dosing schedule. For example, according to a modified CYP2C19 substrate dosing schedule, the CYP2C19 substrate may be administered to the patient at a reduced CYP2C19 substrate dosing frequency. In some such embodiments, the CYP2C19 substrate is omeprazole and the reduced CYP2C19 dosing frequency is once per day; or, alternatively once every other day. As another example, according to a modified CYP2C19 substrate dosing schedule, the CYP2C19 substrate may be administered to the patient to at a reduced CYP2C19 substrate total daily dose. In some such embodiments, the CYP2C19 substrate is omeprazole and the reduced CYP2C19 substrate total daily dose is less than 360 mg per day; alternatively, less than 240 mg per day; alternatively, less than 120 mg per day; alternatively, less than 80 mg per day; alternatively, less than 60 mg per day; alternatively, less than 40 mg per day; or alternatively, less than 20 mg per day.

In one aspect, this disclosure provides a method for treating a gynecological disorder in a patient in need thereof. The method comprises orally administering to the patient sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate ("elagolix sodium"), wherein elagolix sodium is administered in an amount equivalent to 300 mg of elagolix free acid twice daily; wherein the patient receives a once daily dose of 40 mg of omeprazole; and wherein:

(i) a ratio of $C_{max}$ for omeprazole following co-administration of omeprazole with elagolix to $C_{max}$ for omeprazole following administration of omeprazole alone is between about 1.50 and about 2.53, such as about 1.95;

(ii) a ratio of $AUC_{inf}$ for omeprazole following co-administration of omeprazole with elagolix to $AUC_{inf}$ for omeprazole following administration of omeprazole alone is between about 1.39 and about 2.27, such as about 1.78;

(iii) a ratio of $C_{max}$ for omeprazole sulfone following co-administration of omeprazole with elagolix to $C_{max}$ for omeprazole sulfone following administration of omeprazole alone is between about 2.10 and about 3.45, such as about 2.70; and/or (iv) a ratio of $AUC_{inf}$ for omeprazole sulfone following co-administration of omeprazole with elagolix to $AUC_{inf}$ for omeprazole sulfone following administration of omeprazole alone is between about 1.88 and about 3.45, such as about 2.55.

In certain embodiments, where a patient is on a treatment with elagolix sodium for a GnRH related condition and has a second co-morbid condition that requires treatment with omeprazole, a dose adjustment may be required. One embodiment provides a method for management of heavy menstrual bleeding associated with uterine leiomyomas (fibroids), comprising: (i) orally administering to a patient in need thereof elagolix sodium, wherein elagolix sodium is administered in an amount equivalent to 300 mg of elagolix free acid twice daily; and when said patient has a co-morbid Zollinger-Ellison syndrome, said patient receives: (a) a recommended reduced starting daily dose of less than 60 mg of omeprazole administered once a day; (b) a recommended reduced daily dose of less than 80 mg of omeprazole administered once a day, twice a day or three times a day; or (c) a recommended daily reduced dose of less than 120 mg of omeprazole administered three times a day.

Another embodiment provides a method for management of moderate to severe pain associated with endometriosis, comprising: (i) orally administering to a patient in need thereof elagolix sodium, wherein elagolix sodium is administered in an amount equivalent to 150 mg of elagolix free acid once a day or 200 mg of elagolix free acid twice a day; and when said patient has a co-morbid Zollinger-Ellison syndrome, said patient receives (a) a recommended reduced starting daily dose of less than 60 mg of omeprazole administered once a day; (b) a recommended reduced daily dose of less than 80 mg of omeprazole administered once a day, twice a day or three times a day; or (c) a recommended daily reduced dose of less than 120 mg of omeprazole administered three times a day.

In one such embodiment, the recommended reduced starting daily dose of less than 60 mg of omeprazole is greater than 10 mg and less than 60 mg of omeprazole administered once a day. In another such embodiment, the recommended daily reduced dose of 120 mg of omeprazole three times a day is: (a) 120 mg of omeprazole administered two times a day or 120 mg of omeprazole administered once a day; (b) between 10 mg to less than 120 mg of omeprazole administered three times a day; (c) between 10 mg to less than 120 mg of omeprazole administered two times a day; or (d) between 10 mg to less than 120 mg of omeprazole administered once a day.

Yet, another embodiment provides a method for management of heavy menstrual bleeding associated with uterine leiomyomas (fibroids), comprising: orally administering to a patient in need thereof elagolix sodium, wherein elagolix sodium is administered in an amount equivalent to 300 mg of elagolix free acid twice daily; and when the patient has a co-morbid Zollinger-Ellison syndrome, the patient receives a drug that is metabolized by CYP2C19 pathway, such that said drug is (a) lansoprazole, and the recommended reduced daily dose of lansoprazole is less than 60 mg administered once a day, such as 15 mg, 30 mg or 45 mg once a day, or 60 mg every other day; (b) omeprazole, and the recommended reduced daily dose of omeprazole is between 10 mg to less than 360 mg administered daily, such as 10 mg to less than 60 mg every day, or 120 mg twice a day or 120 mg once a day; (c) pantoprazole, and the recommended reduced daily dose of pantoprazole is less than 40 mg twice a day, such as 20 mg twice a day, or 60 mg once a day, or 40 mg once a day; (d) rabeprazole, and the recommended reduced daily dose of rabeprazole is less than 60 mg administered once a day, such as 5 mg or 10 mg or 20 mg or 40 mg or 50 mg once a day; or (e) esomoprazole, and the recommended reduced daily dose of esomoprazole is less than 40 mg twice a day, such as 20 mg twice a day or 30 mg once a day or 40 mg once a day.

Another embodiment provides a method for management of moderate to severe pain associated with endometriosis, comprising: orally administering to a patient in need thereof elagolix sodium, wherein elagolix sodium is administered in an amount equivalent to 150 mg of elagolix free acid once a day or 200 mg of elagolix free acid twice a day; and when the patient has a co-morbid Zollinger-Ellison syndrome, the patient receives a drug that is metabolized by CYP2C19 pathway, such that said drug is (a) lansoprazole, and the recommended reduced daily dose of lansoprazole is less than 60 mg administered once a day, such as 15 mg, 30 mg or 45 mg once a day, or 60 mg every other day; (b) omeprazole, and the recommended reduced daily dose of omeprazole is between 10 mg to less than 360 mg administered daily, such as 10 mg to less than 60 mg every day, or 120 mg twice a day or 120 mg once a day; (c) pantoprazole, and the recommended reduced daily dose of pantoprazole is less than 40 mg twice a day, such as 20 mg twice a day, or 60 mg once a day, or 40 mg once a day; (d) rabeprazole, and the recommended reduced daily dose of rabeprazole is less than 60 mg administered once a day, such as 5 mg or 10 mg or 20 mg or 40 mg or 50 mg once a day; or (e) esomoprazole, and the recommended reduced daily dose of esomoprazole is less than 40 mg twice a day, such as 20 mg twice a day or 30 mg once a day or 40 mg once a day.

In any aspect or embodiment described herein, the gynecological disorder may be endometriosis, uterine fibroids, polycystic ovary syndrome (PCOS), or adenomyosis. In any aspect or embodiment described herein, the method may be for the management of certain signs and/or symptoms of the gynecological disorder. For example, in certain embodiments, the method is for the management of moderate to severe pain associated with endometriosis. As another example, in certain embodiments, the method is for the management of heavy menstrual bleeding associated with uterine fibroids.

BRIEF DESCRIPTION OF THE DRAWINGS

FIG. 1 shows the study design of bupropion DDI with elagolix sodium.

DETAILED DESCRIPTION

Figure 2:
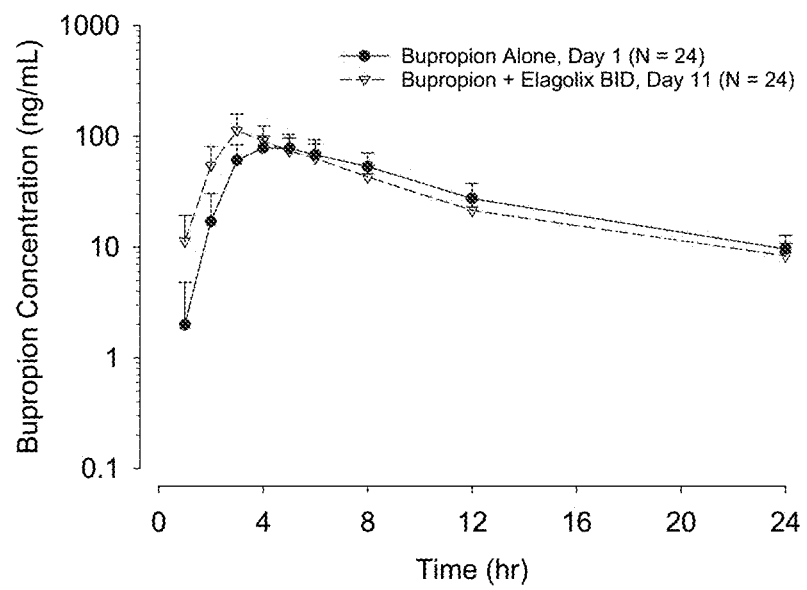
FIG. 2 shows mean bupropion and OH-bupropion plasma concentration-time profiles.
Figure 2:
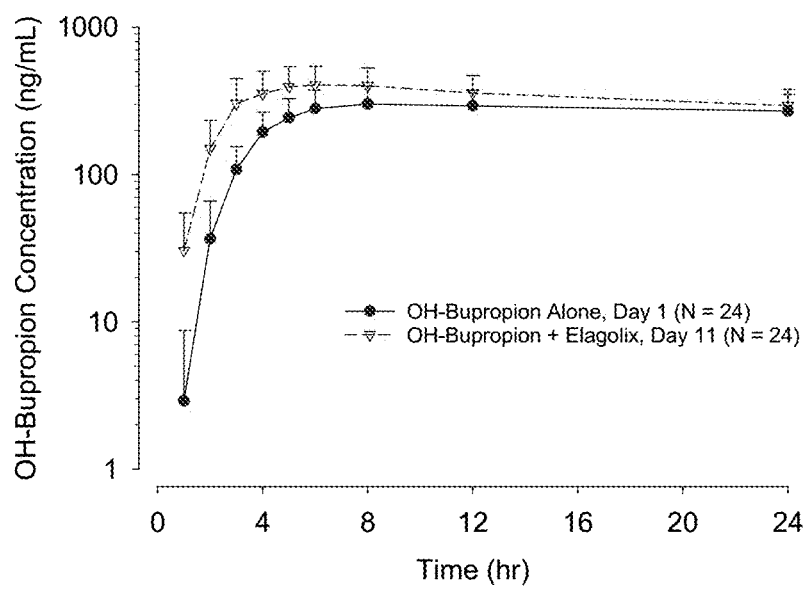

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. DEFINITIONS

As used in the specification and the appended claims, unless specified to the contrary, the following terms have the meaning indicated:

The term "about" as used herein, means approximately, and in most cases within 10% of the stated value.

The term "co-administered" or "co-administration" refers to concomitant administration of two or more active agents such that one active agent is given in the presence of another active agent. The active agents may be, but need not be, administered in a substantially simultaneous manner (e.g., within about 5 min of each other), in a sequential manner, or both. It is contemplated, for example, that co-administration may include administering one active agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient.

The term "pharmaceutically acceptable" is used adjectivally to mean that the modified noun is appropriate for use as a pharmaceutical product for human use or as a part of a pharmaceutical product for human use.

The term "pharmacokinetic parameter(s)" refers to any suitable pharmacokinetic parameter, such as $T_{max}$, $C_{max}$, and AUC. The term "$C_{max}$" refers to the peak concentration and, in particular, the maximum observed plasma/serum concentration of drug. The term "$T_{max}$" refers to the time to reach the peak concentration. The term "$AUC_t$," refers to the area under the plasma concentration-time curve, where t is the time of the last measurable plasma concentration in the study. The term "AUC." refers to the area under the plasma concentration-time curve from time zero to infinity following a single dose.

The terms "treat", "treating" and "treatment" refer to a method of alleviating or abrogating a condition, disorder, or disease and/or the attendant symptoms thereof.

B. GNRH RECEPTOR ANTAGONISTS

Elagolix is a non-peptide GnRH receptor antagonist approved for management of pain associated with endometriosis; and in development for treatment of heavy menstrual bleeding due to uterine fibroids.

Elagolix (free acid) has the following structure:

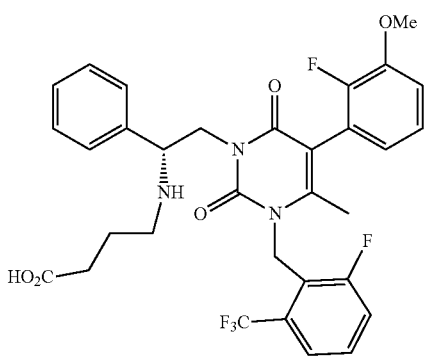 [SMILES: COc1cccc(-c2c(C)n(Cc3c(F)cccc3C(F)(F)F)c(=O)n(C[C@H](NCCCC(=O)O)c3ccccc3)c2=O)c1F]

Elagolix (free acid) is also known as 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid.

Elagolix is typically provided as elagolix sodium, which has the molecular structure $C_{32}H_{29}F_5N_3O_5Na$, a molecular weight of 653.58, and the following structure:

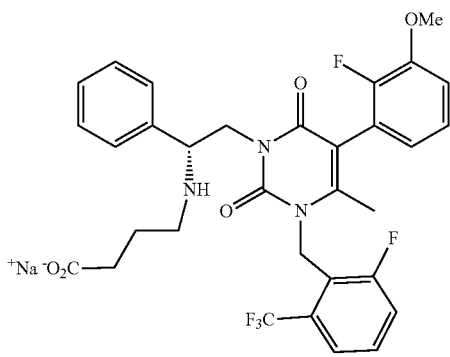

Elagolix sodium is also known sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate.

U.S. Pat. No. 7,056,927, which is incorporated herein by reference in its entirety, describes elagolix and pharmaceutically acceptable salts thereof.

Elagolix is eliminated with an apparent terminal phase elimination half-life ($t_{1/2}$) of approximately 4 to 6 hours, allowing for once or twice daily dosing. For example, An exemplary recommended elagolix dosing schedule for the management of moderate to severe pain associated with endometriosis is 150 mg once daily. Alternatively, another recommended elagolix dosing schedule for the management of moderate to severe pain associated with endometriosis is 200 mg twice daily. As another example, an exemplary recommended elagolix dosing schedule for the management of heavy menstrual bleeding associated with uterine leiomyomas (fibroids) is 300 mg twice daily.

C. CO-ADMINISTRATION WITH A CYP2B6 SUBSTRATE

In one aspect, this disclosure provides a method for treating a gynecological disorder in a patient in need thereof. The method comprises orally administering to the patient sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate ("elagolix sodium"), wherein the patient concomitantly receives treatment with a CYP2B6 substrate. In certain embodiments, the CYP2B6 substrate is bupropion.

Bupropion is typically provided as bupropion hydrochloride, which has the molecular structure $C13H_{18}ClNO·HCl$, a molecular weight of 276.2, and the following structure:

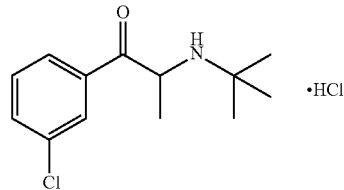 [SMILES: CC(NC(C)(C)C)C(=O)c1cccc(Cl)c1 ; Cl]

Bupropion hydrochloride is also known as (±)-1-(3-chlorophenyl)-2-[(1,1-dimethylethyl)amino]-1-propanone hydrochloride.

U.S. Pat. No. 3,885,046, which is incorporated herein by reference in its entirety, describes bupropion and pharmaceutically acceptable salts thereof.

Bupropion is primarily metabolized to hydroxybupropion by CYP2B6. Thus, it is commonly believed that if bupropion is used concomitantly with a CYP2B6 inducer, it may be necessary to increase the dose of bupropion. See WELLBUTRIN® (bupropion hydrochloride) Prescribing Information (dated 05-2017).

In vitro studies had indicated that elagolix is a weak to moderate inducer of CYP2B6. Thus, it was believed that elagolix has the potential to decrease the exposure of CYP2B6 sensitive substrates. Instead, during the course of drug-drug interaction studies, it was surprisingly discovered that changes in bupropion (a CYP2B6 substrate) exposure upon co-administration with elagolix were not considered clinically relevant. Moreover, $C_{max}$ values for bupropion and its metabolite, hydroxybupropion, increased upon co-administration with elagolix.

Data provided herein demonstrate that co-administration of elagolix sodium and bupropion results in an increased bupropion $C_{max}$ relative to administration of bupropion alone. In particular, a single 150 mg dose of bupropion given in the presence of elagolix (e.g., elagolix sodium administered twice daily in an amount equivalent to 300 mg of elagolix free acid for 2-14, preferably 10, preceding days) provides a bupropion $C_{max}$ ratio, which compares (A) bupropion $C_{max}$ when co-administered with elagolix to (B) bupropion $C_{max}$ when administered alone (A/B), of 1.246 (1.104-1.407).

Data provided herein also demonstrate that co-administration of elagolix sodium and bupropion does not produce a clinically meaningful change bupropion $AUC_{inf}$ relative to administration of bupropion alone. In particular, a single 150 mg dose of bupropion given in the presence of elagolix (e.g., elagolix sodium administered twice daily in an amount equivalent to 300 mg of elagolix free acid for 2-14, preferably 10, preceding days) provides a bupropion $AUC_{inf}$ ratio, which compares (A) bupropion $AUC_{inf}$ when co-administered with elagolix to (B) bupropion $AUC_{inf}$ when administered alone (A/B), of 0.965 (0.910-1.023).

This discovery allows the possibility of maintaining or reducing the recommended bupropion dosage amounts and/or maintaining or decreasing the recommended bupropion dosing frequency. In particular, an exemplary recommended bupropion dosing schedule, such as 150 mg BID, may be maintained or modified by decreasing the total daily dosage amount, such as by reducing the amount of each dose and/or decreasing the dosing frequency (e.g., from twice daily to once daily).

Bupropion (typically provided as bupropion hydrochloride) is indicated for the treatment of major depressive disorder (MDD), prevention of seasonal affective disorder (SAD), and as an aid to smoking cessation treatment. Bupropion hydrochloride products are available as immediate-, sustained-, and extended-release formulations.

An exemplary recommended immediate-release bupropion dosing schedule for the treatment of MDD includes a starting dose of 100 mg twice daily to provide a bupropion total daily dose of 200 mg; the bupropion total daily dose may be increased to 300 mg, given as 100 mg three times daily with an interval of at least 6 hours between doses; alternatively, the bupropion total daily dose may be increased to 450 mg, given as 150 mg three times daily. In patients with moderate to severe hepatic impairment, an exemplary recommended immediate-release bupropion dosing schedule for the treatment of MDD is 75 mg once daily.

An exemplary recommended sustained-release bupropion dosing schedule for the treatment of MDD includes a starting dose of 150 mg once daily; the bupropion total daily dose may be increased to 300 mg, given as 150 mg twice times daily with an interval of at least 8 hours between successive doses; alternatively, the bupropion total daily dose may be increased to 400 mg, given as 200 mg twice daily. In patients with impaired hepatic function, an exemplary recommended sustained-release bupropion dosing schedule for the treatment of MDD is 100 mg once daily or 150 mg every other day.

An exemplary recommended sustained-release bupropion dosing schedule as an aid to smoking cessation treatment includes a starting dose of 150 mg once daily; the bupropion total daily dose may be increased to 300 mg, given as 150 mg twice times daily with an interval of at least 8 hours between doses. In patients with moderate to severe hepatic impairment, an exemplary recommended sustained-release bupropion dosing schedule as an aid to smoking cessation treatment is 150 mg given every other day.

An exemplary recommended extended-release bupropion dosing schedule for the treatment of MDD includes a starting dose of 150 mg once daily, which may be increased to a dose of 300 mg once daily. Likewise, an exemplary recommended extended-release bupropion dosing schedule for the prevention of SAD includes a starting dose of 150 mg once daily, which may be increased to a dose of 300 mg once daily. In patients with moderate to severe hepatic impairment, an exemplary recommended extended-release bupropion dosing schedule for the treatment of MDD or the prevention of SAD is 150 mg once daily.

Alternatively, an exemplary recommended extended-release bupropion dosing schedule for the treatment of MDD is 450 mg once daily.

In certain embodiments, no dose adjustment is needed for bupropion when co-administered with elagolix sodium. Thus, bupropion may administered according to a recommended bupropion dosing schedule, such as a recommended immediate-release bupropion dosing schedule, a recommended sustained-release bupropion dosing schedule, or a recommended extended-release bupropion dosing schedule.

In certain embodiments, a dose adjustment is needed for bupropion when co-administered with elagolix sodium. Thus, bupropion may be administered according to a modified dosing schedule. Exemplary modified bupropion dosing schedules may involve increasing the time between bupropion doses, such as going from BID to QD or from QD to every other day and/or reducing the total daily dose of bupropion, such as from 300 mg to 250 mg, 200 mg, 150 mg, 100 mg, 50 mg, or integer multiples therebetween.

In some such embodiments, a modified bupropion dosing schedule provides a ratio of $C_{max}$ for bupropion following co-administration of bupropion according to the modified bupropion dosing schedule with elagolix according to a recommended elagolix dosing schedule to $C_{max}$ for bupropion following administration of bupropion alone according to a recommended bupropion dosing schedule, wherein the ratio is between about 0.5 and about 2.0; or alternatively, between about 0.8 and about 1.25 and/or a ratio of $AUC_{inf}$ for bupropion following co-administration of bupropion according to the modified bupropion dosing schedule with elagolix according to a recommended elagolix dosing schedule to $AUC_{inf}$ for bupropion following administration of bupropion alone according to a recommended bupropion dosing schedule, wherein the ratio is between about 0.5 and about 2.0; or alternatively, between about 0.8 and about 1.25.

D. CO-ADMINISTRATION WITH A CYP2C19 SUBSTRATE

In one aspect, this disclosure provides a method for treating a gynecological disorder in a patient in need thereof. The method comprises orally administering to the patient sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino) butanoate ("elagolix sodium"), wherein the patient concomitantly receives treatment with a CYP2C19 substrate. In certain embodiments, the CYP2C19 substrate is omeprazole.

Omeprazole has the molecular structure $C_{17}H_{19}N_3O_3S$, a molecular weight of 345.42, and the following structure:

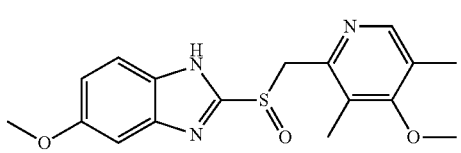

Omeprazole is also known as 5-methoxy-2-[[(4-methoxy3,5-dimethyl-2-pyridinyl) methyl] sulfinyl]-1H-benzimidazole.

U.S. Pat. No. 4,255,431, which is incorporated herein by reference in its entirety, describes omeprazole.

Omeprazole is metabolized via multiple pathways, including CYP2C19-mediated formation of 5-hydroxyomeprazole and CYP3A-mediated formation of omeprazole sulfone. Drugs that induce CYP2C19 or CYP3A4 may substantially decrease omeprazole concentrations. See PRILOSEC® (omeprazole) Prescribing Information (dated 09-2012).

Omeprezole (PRILOSEC®) is indicated for the long-term treatment of pathological hypersecretory conditions (e.g., Zollinger-Ellison syndrome, multiple endocrine adenomas and systemic mastocytosis) in adults. Starting dose for this condition is 60 mg once daily (varies with individual patient, as long as clinically indicated. Daily doses of greater than 80 mg should be administered in divided doses. Moreover, doses up to 120 mg three times daily have been administered for this condition. Some Zollinger-Ellison syndrome have been treated continuously for more than 5 years. See Prescribing Information (dated 09-2012).

In vitro studies had indicated that elagolix is a weak to moderate inducer of CYP3A4 and a weak inhibitor of CYP2C19. During the course of drug-drug interaction studies, it was discovered that no dose adjustments are needed for omeprazole at doses of 40 mg once daily or lower when co-administered with elagolix, though $C_{max}$ and $AUC_{inf}$ values for omeprazole and its metabolite, omeprazole sulfone, increased upon co-administration with elagolix.

Data provided herein demonstrate that co-administration of elagolix sodium and omeprazole results in an increased omeprazole $AUC_{inf}$ and $C_{max}$ relative to administration of omeprazole alone. In particular, a single 40 mg dose of omeprazole given in the presence of elagolix (e.g., elagolix sodium administered twice daily in an amount equivalent to 300 mg of elagolix free acid for 2-14, preferably 9, preceding days) provides an omeprazole $AUC_{inf}$ ratio, which compares (A) omeprazole $AUC_{inf}$ when co-administered with elagolix to (B) omeprazole $AUC_{inf}$ when administered alone (A/B), of 1.78 (1.39-2.27). In addition, a single 40 mg dose of omeprazole given in the presence of elagolix (e.g., elagolix sodium administered twice daily in an amount equivalent to 300 mg of elagolix free acid for 2-14, preferably 9, preceding days) provides an omeprazole $C_{max}$ ratio, which compares (A) omeprazole $C_{max}$ when co-administered with elagolix to (B) omeprazole $C_{max}$ when administered alone (A/B), of 1.95 (1.50-2.53).

This discovery allows the possibility of maintaining the recommended omeprazole dosage amounts of 40 mg per day or less, while reducing the recommended omeprazole dosage amounts of 60 mg per day or more and/or decreasing the dosing frequency (e.g., from three times daily to twice daily) for such higher doses. In particular, an exemplary recommended omeprazole dosing schedule, such as 120 mg given three times daily for a total daily dose of 360 mg, may be modified by decreasing the total daily dosage amount, such as by reducing the amount of each dose and/or decreasing the dosing frequency (e.g., from three times daily to twice daily).

Omeprazole is indicated for the treatment of active duodenal ulcer, the eradication of Helicobacter pylori to reduce the risk of duodenal ulcer recurrence, the treatment of active benign gastric ulcer, the treatment of gastroesophageal reflux disease (GERD), the treatment of erosive esophagitis (EE) due to acid-mediated GERD, the maintenance of healing of EE due to acid-mediated GERD, and pathologic hypersecretory conditions (e.g., Zollinger-Ellison syndrome, multiple endocrine adenomas and systemic mastocytosis).

An exemplary recommended omeprazole dosing schedule for treatment of active duodenal ulcer is 20 mg once daily. An exemplary recommended omeprazole dosing schedule for the eradication of Helicobacter pylori to reduce the risk of duodenal ulcer recurrence is 20 mg once daily; alternatively, 40 mg once daily. An exemplary recommended omeprazole dosing schedule for treatment of active benign gastric ulcer is 40 mg once daily. An exemplary recommended omeprazole dosing schedule for treatment of symptomatic GERD is 20 mg once daily. An exemplary recommended omeprazole dosing schedule for treatment of EE due to acid-mediated GERD is 20 mg once daily. An exemplary recommended omeprazole dosing schedule for maintenance of healing of EE due to acid-mediated GERD is 20 mg once daily. An exemplary recommended omeprazole dosing schedule for pathological hypersecretory conditions is 60 mg once daily; alternatively, up to 120 mg three times daily (daily dosages greater than 80 mg should be administered as divided doses).

In certain embodiments, no dose adjustment is needed for omeprazole at total daily doses of 40 mg or less when co-administered with elagolix sodium. Thus, omeprazole may administered according to a recommended omeprazole dosing schedule, such as a recommended omeprazole dosing schedule for treatment of active duodenal ulcer, a recommended omeprazole dosing schedule for the eradication of Helicobacter pylori to reduce the risk of duodenal ulcer recurrence, a recommended omeprazole dosing schedule for treatment of active benign gastric ulcer, a recommended omeprazole dosing schedule for treatment of symptomatic GERD, a recommended omeprazole dosing schedule for treatment of EE due to acid-mediated GERD, or a recommended omeprazole dosing schedule for maintenance of healing of EE due to acid-mediated GERD.

In certain embodiments, a dose adjustment is needed for omeprazole when co-administered with elagolix sodium, particularly for higher doses of omeprazole, such as for pathologic hypersecretory conditions (e.g., Zollinger-Ellison syndrome). Thus, omeprazole may be administered according to a modified omeprazole dosing schedule. Exemplary modified omeprazole dosing schedules may involve increasing the time between omeprazole doses, such as going from three times daily to BID or from BID to QD and/or reducing the total daily dose of omeprazole, such as from 360 mg to 300 mg, 240 mg, 180 mg, 120 mg, 60 mg, or integer multiples therebetween.

In some such embodiments, a modified omeprazole dosing schedule provides a ratio of $C_{max}$ for omeprazole following co-administration of omeprazole according to the modified omeprazole dosing schedule with elagolix according to a recommended elagolix dosing schedule to $C_{max}$ for omeprazole following administration of omeprazole alone according to a recommended omeprazole dosing schedule, wherein the ratio is between about 0.5 and about 2.0; or alternatively, between about 0.8 and about 1.25 and/or a ratio of $AUC_{inf}$ for omeprazole following co-administration of omeprazole according to the modified omeprazole dosing schedule with elagolix according to a recommended elagolix dosing schedule to $AUC_{inf}$ for omeprazole following administration of omeprazole alone according to a recommended omeprazole dosing schedule, wherein the ratio is between about 0.5 and about 2.0; or alternatively, between about 0.8 and about 1.25.

In certain embodiments, where a patient is on a treatment with elagolix sodium for a GnRH related condition and has a second co-morbid condition that requires treatment with omeprazole, a dose adjustment may be required. One embodiment provides a method for management of heavy menstrual bleeding associated with uterine leiomyomas (fibroids), comprising: (i) orally administering to a patient in need thereof elagolix sodium, wherein elagolix sodium is administered in an amount equivalent to 300 mg of elagolix free acid twice daily; and when said patient has a co-morbid Zollinger-Ellison syndrome, said patient receives: (a) a recommended reduced starting daily dose of less than 60 mg of omeprazole administered once a day; (b) a recommended reduced daily dose of less than 80 mg of omeprazole administered once a day, twice a day or three times a day; or (c) a recommended daily reduced dose of less than 120 mg of omeprazole administered three times a day.

Another embodiment provides a method for management of moderate to severe pain associated with endometriosis, comprising: (i) orally administering to a patient in need thereof elagolix sodium, wherein elagolix sodium is administered in an amount equivalent to 150 mg of elagolix free acid once a day or 200 mg of elagolix free acid twice a day; and when said patient has a co-morbid Zollinger-Ellison syndrome, said patient receives (a) a recommended reduced starting daily dose of less than 60 mg of omeprazole administered once a day; (b) a recommended reduced daily dose of less than 80 mg of omeprazole administered once a day, twice a day or three times a day; or (c) a recommended daily reduced dose of less than 120 mg of omeprazole administered three times a day.

In one such embodiment, the recommended reduced starting daily dose of less than 60 mg of omeprazole is greater than 10 mg and less than 60 mg of omeprazole administered once a day, or integer multiples there between. In another such embodiment, the recommended daily reduced dose of 120 mg of omeprazole three times a day is: (a) 120 mg of omeprazole administered two times a day or 120 mg of omeprazole administered once a day; (b) between 10 mg to less than 120 mg of omeprazole administered three times a day or integer multiples there between; (c) between 10 mg to less than 120 mg of omeprazole administered two times a day or integer multiples there between; or (d) between 10 mg to less than 120 mg of omeprazole administered once a day or integer multiples there between.

Yet, another embodiment provides a method for management of heavy menstrual bleeding associated with uterine leiomyomas (fibroids), comprising: orally administering to a patient in need thereof elagolix sodium, wherein elagolix sodium is administered in an amount equivalent to 300 mg of elagolix free acid twice daily; and when the patient has a co-morbid Zollinger-Ellison syndrome, the patient receives a drug that is metabolized by CYP2C19 pathway, such that said drug is (a) lansoprazole, and the recommended reduced daily dose of lansoprazole is less than 60 mg administered once a day, such as 15 mg, 30 mg or 45 mg once a day, or 60 mg every other day or integer multiples there between; (b) omeprazole, and the recommended reduced daily dose of omeprazole is between 10 mg to less than 360 mg administered daily, such as 10 mg to less than 60 mg every day, or 120 mg twice a day or 120 mg once a day or integer multiples there between; (c) pantoprazole, and the recommended reduced daily dose of pantoprazole is less than 40 mg twice a day, such as 20 mg twice a day, or 60 mg once a day, or 40 mg once a day or integer multiples there between; (d) rabeprazole, and the recommended reduced daily dose of rabeprazole is less than 60 mg administered once a day, such as 5 mg or 10 mg or 20 mg or 40 mg or 50 mg once a day or integer multiples there between; or (e) esomoprazole, and the recommended reduced daily dose of esomoprazole is less than 40 mg twice a day, such as 20 mg twice a day or 30 mg once a day or 40 mg once a day or integer multiples there between.

Another embodiment provides a method for management of moderate to severe pain associated with endometriosis, comprising: orally administering to a patient in need thereof elagolix sodium, wherein elagolix sodium is administered in an amount equivalent to 150 mg of elagolix free acid once a day or 200 mg of elagolix free acid twice a day; and when the patient has a co-morbid Zollinger-Ellison syndrome, the patient receives a drug that is metabolized by CYP2C19 pathway, such that said drug is (a) lansoprazole, and the recommended reduced daily dose of lansoprazole is less than 60 mg administered once a day, such as 15 mg, 30 mg or 45 mg once a day, or 60 mg every other day or integer multiples there between; (b) omeprazole, and the recommended reduced daily dose of omeprazole is between 10 mg to less than 360 mg administered daily, such as 10 mg to less than 60 mg every day, or 120 mg twice a day or 120 mg once a day or integer multiples there between; (c) pantoprazole, and the recommended reduced daily dose of pantoprazole is less than 40 mg twice a day, such as 20 mg twice a day, or 60 mg once a day, or 40 mg once a day or integer multiples there between; (d) rabeprazole, and the recommended reduced daily dose of rabeprazole is less than 60 mg administered once a day, such as 5 mg or 10 mg or 20 mg or 40 mg or 50 mg once a day or integer multiples there between; or (e) esomoprazole, and the recommended reduced daily dose of esomoprazole is less than 40 mg twice a day, such as 20 mg twice a day or 30 mg once a day or 40 mg once a day or integer multiples there between.

E. GENERAL CONSIDERATIONS

In any aspect or embodiment employing a modified dosing schedule (e.g., a modified CYP2B6 substrate dosing schedule or a modified CYP2C19 substrate dosing schedule), the modification to the recommended dosing schedule can involve reducing the recommended total daily dose, such as by reducing the amount of CYP2B6 substrate or CYP2C19 substrate administered for each dose and/or reducing the frequency of administration (increasing the dosing interval), such as from three times daily to twice daily, or from twice daily to once daily, or from once daily to once every other day.

In any aspect or embodiment employing a modified dosing schedule (e.g., a modified CYP2B6 substrate dosing schedule or a modified CYP2C19 substrate dosing schedule), the modification to the recommended dosing schedule can be done for a period of time but does not have to stay fixed. Nor does the modified dosing schedule need to be reduced to a fixed schedule. Specifically enumerated modified dosing schedules are provided only as examples and are not meant to be limiting. The prescribing physician or patient has the option of reducing to any lower dose and/or increasing the period between doses for as long as needed, after which time they can adjust to a new modified dosing schedule or revert back to a recommended dosing schedule. This provides maximum flexibility for the patient and/or physician to titrate the drug to his or her individual need and at their discretion.

Pharmacokinetic parameters described herein should be measured in accordance with standards and practices which would be acceptable to a pharmaceutical regulatory agency such as FDA, EMA, MHLW, or WHO. The values may be based on measurements taken at appropriate intervals following the time of ingestion, such as every hour, or at increasingly sparse sampling intervals, such as 2, 4, 6, 8, 10, 12, 16, and 24 hours after ingestion. The pharmacokinetic parameters can be assessed either following a single-dose of drug or at steady state, preferably following a single-dose. In certain embodiments, pharmacokinetic parameters are determined following a single dose of the CYP2B6 substrate or CYP2C19 substrate.

In some such embodiments, pharmacokinetic parameters are determined following a single dose of the CYP2B6 substrate or CYP2C19 substrate co-administered in the presence of elagolix, preferably administered according to a recommended elagolix dosing schedule, such as 150 mg QD, 200 mg BID, or 300 mg BID, over a period of time to achieve steady state. The pharmacokinetic parameters can be assessed under fasting or fed conditions, preferably under fasting conditions.

In aspect or embodiment described herein, any of the above methods further comprise administering to the subject a hormone to reduce or alleviate potential side effects of elagolix. For example, the method may comprise administration of an estrogen, a progestin, or a combination thereof. Such treatments are commonly referred to as "add-back" therapy.

In some such embodiments, the add-back therapy comprises a progestogen, such as a progestin. In some such embodiments, the add-back therapy comprises an estrogen. In some such embodiments, the add-back therapy comprises a progestin and an estrogen.

The estrogen and/or progestogen can be administered orally, transdermally or intravaginally. Suitable progestogens for use in the add-back therapy include, for example, progesterone, norethindrone, norethindrone acetate, norgestimate, drospirenone, and medroxyprogestogen. Suitable estrogens for use in the add-back therapy include, for example, estradiol, ethinyl estradiol, and conjugated estrogens. Combined oral formulations containing an estrogen and a progestogen are known in the art and include, for example, Activella®, Angeliq®, FemHRT®, Jenteli™, Mimvey™, Prefest™, Premphase®, and Prempro®.

In certain embodiments, the estrogen is estradiol, ethinyl estradiol, or a conjugated estrogen. In some such embodiments, the estrogen is estradiol. In some such embodiments, the estradiol is administered once a day. In some such embodiments, the dose of estradiol is 0.5 mg. In other such embodiments, the dose of estradiol is 1.0 mg.

In certain embodiments, the progestogen is progesterone, norethindrone, norethindrone acetate, norgestimate, medroxyprogesterone, or drospirenone. In some such embodiments, the progestogen is norethindrone acetate. In some such embodiments, the norethindrone acetate is administered once a day. In some such embodiments, the dose of norethindrone acetate is 0.1 mg. In some such embodiments, the dose of norethindrone acetate is 0.5 mg.

In certain embodiments, the add-back therapy comprises a norethisterone prodrug, such as norethindrone acetate. In some such embodiments, the add-back therapy further comprises estradiol. Thus, in some such embodiments, the add-back therapy comprises estradiol and norethindrone acetate. In some such embodiments, estradiol and norethindrone acetate are administered orally once per day. In some such embodiments, estradiol is administered in an amount of about 0.5 mg and norethindrone acetate is administered in an amount of about 0.1 mg per day. In other such embodiments, estradiol is administered in an amount of about 1.0 mg and norethindrone acetate is administered in an amount of about 0.5 mg per day.

In certain embodiments, the dose of elagolix sodium is administered twice a day and add-back therapy is administered once a day. In some such embodiments, a dose of elagolix sodium is administered in the morning with add-back therapy, such as a combination of an estrogen and a progestogen (e.g., estradiol and norethindrone acetate) and a dose of elagolix sodium is administered in the evening without add-back therapy.

In certain embodiments, elagolix sodium is present in a fixed dose combination with the add-back therapy. For example, a capsule may contain a caplet or tablet comprising elagolix sodium and a caplet or tablet comprising the add-back therapy, such as a combination of an estrogen and a progestogen (e.g., estradiol and norethindrone acetate). In some such embodiments, the capsule comprises about 310.9 mg elagolix sodium (equivalent to 300 mg elagolix free acid), 1 mg estradiol, and 0.5 mg norethindrone acetate.

The pharmaceutical compositions, methods, and uses described herein will be better understood by reference to the following exemplary embodiments and examples, which are included as an illustration of and not a limitation upon the scope of the invention.

F. EXAMPLES

Example 1: Co-Administration with a CYP2B6 Substrate

A drug-drug interaction (DDI) study assessed the impact of elagolix sodium on the pharmacokinetics (PK) of a CYP2B6 substrate (bupropion) in healthy premenopausal female volunteers. In particular, the objective of this DDI study was to evaluate the effect of multiple doses of elagolix sodium on the pharmacokinetics of bupropion and its major metabolite, hydroxybupropion (OH-bupropion), in healthy premenopausal female subjects.

Subjects: Twenty four (24) adult premenopausal women in generally good health participated in this study. Subjects were 23.0 to 49.0 years of age and had a body mass index ≥19.5 and <29.9 kg/m$^2$. Subjects were excluded if they had positive test results for hepatitis A, B, or C or for HIV infection or using known CYP3A inhibitors or inducers or P-glycoprotein inhibitors or OATP inhibitors or digoxin within 1 month prior to study drug administration. Subjects not used oral contraception or has not taken an oral estrogen or oral progestin preparation within the 14 days prior to study drug administration. Subjects were not to have consumed alcohol, grapefruit, Seville oranges, star fruit, or quinine/tonic water within 72 hours of the first drug dose and during the study, or nicotine-containing products within 6 months before study drug administration and during the study.

TABLE 1

| Subject Demographic Characteristics | |
|---|---|
| Characteristic | Value (n = 24) |
| Age, years$^a$ | 37.0 ± 8.66 (23-49) |
| Weight, kg$^a$ | 67.5 ± 10.61 (45.5-88.5) |
| BMI (kg/m$^2$)$^a$ | 25.4 ± 3.45 (19.5-29.9) |

TABLE 1-continued

Subject Demographic Characteristics

| Characteristic | Value (n = 24) |
| --- | --- |
| Race, n (%) | |
| White/Caucasian | 8 (33.3%) |
| Black | 13 (54.2%) |
| Asian | 1 (4.2%) |
| Multi Race | 2 (8.3%) |

[a]Arithmetic Mean ± standard deviation (range)

Methods: In a single-sequence, two-period study, healthy women received single oral doses of 150 mg bupropion (extended-release tablets) in the morning on day 1 in period 1 and on day 11 in period 2. Elagolix 300 mg BID (as 300 mg immediate release tablets) was administered in the morning and evening on days 1 through 14 in period 2. The study design is shown in FIG. 1. The doses of bupropion and elagolix were taken orally in the morning after at least an 8-hour fast with approximately 240 mL of water, breakfast was consumed 2 hours after dosing. No food was consumed for 2 hours prior to the evening doses of elagolix continuing through 2 hours after. The doses of elagolix were separated by approximately 12 hours.

Intensive PK sampling was performed for bupropion (parent) and OH-bupropion (metabolite) when bupropion dosed alone and with elagolix.

Plasma concentrations of bupropion, OH-bupropion, and elagolix were determined using validated liquid chromatography methods with tandem mass spectrometric detection.

Individual PK parameters (peak concentration [$C_{max}$] and area under the concentration-time curve [AUC]) were estimated using noncompartmental methods. The pharmacokinetic parameters included $C_{max}$, time to $C_{max}$ ($T_{max}$), area under the plasma concentration-time curve (AUC; $AUC_t$ and $AUC_{inf}$ for bupropion and OH-bupropion).

A linear mixed effects repeated measures analysis was performed for $T_{max}$ and the natural logarithms of $C_{max}$ and AUC to assess the effect of elagolix on bupropion utilizing data from Period 1 Day 1 (bupropion alone) and Period 2 Day 11 (bupropion in combination with elagolix). A similar analysis was conducted for the OH-bupropion and ratio of OH-bupropion to bupropion AUCs.

Central value ratios (90% confidence intervals) for $C_{max}$, AUC, and metabolite to parent ratios (MPRs) (day 11, period 2 vs. day 1, period 1) were calculated to assess the DDIs. Safety was evaluated through assessment of adverse events, vital signs, electrocardiogram, and clinical laboratory tests.

Adverse events (AEs) were monitored throughout the DDI study. Additional safety evaluations included monitoring of physical examinations, vital signs, electrocardiogram variables, and clinical laboratory values were assessed Results: The co-administration of bupropion with elagolix resulted in no/minimal changes (≤12%) in AUC values and MPRs, and 25% and 32% increase in $C_{max}$ values of bupropion and OH-bupropion, respectively. There were no new or unexpected safety findings in the study.

Table 2 and FIG. 2 show the pharmacokinetic parameters and the concentration-time profiles for bupropion and its metabolite when administered alone and with elagolix.

TABLE 2

Pharmacokinetic Parameters of Bupropion and Metabolite

| | Bupropion | | OH-Bupropion | |
| --- | --- | --- | --- | --- |
| Pharmacokinetic Parameter (unit) | Bupropion Alone (Day 1, Period 1) (N = 24) | Bupropion + Elagolix (Day 11, Period 2) (N = 24) | Bupropion Alone (Day 1, Period 1) (N = 24) | Bupropion + Elagolix (Day 11, Period 2) (N = 24) |
| $T_{max}{}^a$ (h) | 4.0 (3.0-8.0) | 3.0 (3.0-5.0) | 10.0 (6.0-24.0) | 6.0 (5.0-12.0) |
| $C_{max}{}^b$ (ng/mL) | 89.5 (26) | 115 (39) | 323 (30) | 429 (33) |
| $AUC_t{}^b$ (ng · h/mL) | 1090 (29) | 1060 (27) | 15700 (33) | 17000 (32) |
| $AUC_{inf}{}^b$ (ng · h/mL) | 1130 (29) | 1090 (27) | 16700 (35) | 17600 (33) |
| $t_{1/2}{}^c$ (h) | 28.0 (7.45) | 25.9 (6.55) | 24.7 (6.06) | 20.5 (4.46) |
| Metabolite to Parent $C_{max}$ Ratio[a] | — | — | 3.61 (1.66-6.72) | 3.92 (1.65-6.74) |
| Metabolite to Parent $AUC_t$ Ratio[a] | — | — | 15.4 (7.65-25.6) | 15.9 (8.94-28.7) |
| Metabolite to Parent $AUC_{inf}$ Ratio[a] | — | — | 15.7 (7.75-25.0) | 15.9 (8.97-28.2) |

[a]Median (Minimum-Maximum)
[b]Mean (% CV)
[c]Harmonic mean (pseudo-standard deviation)

Figure 3:
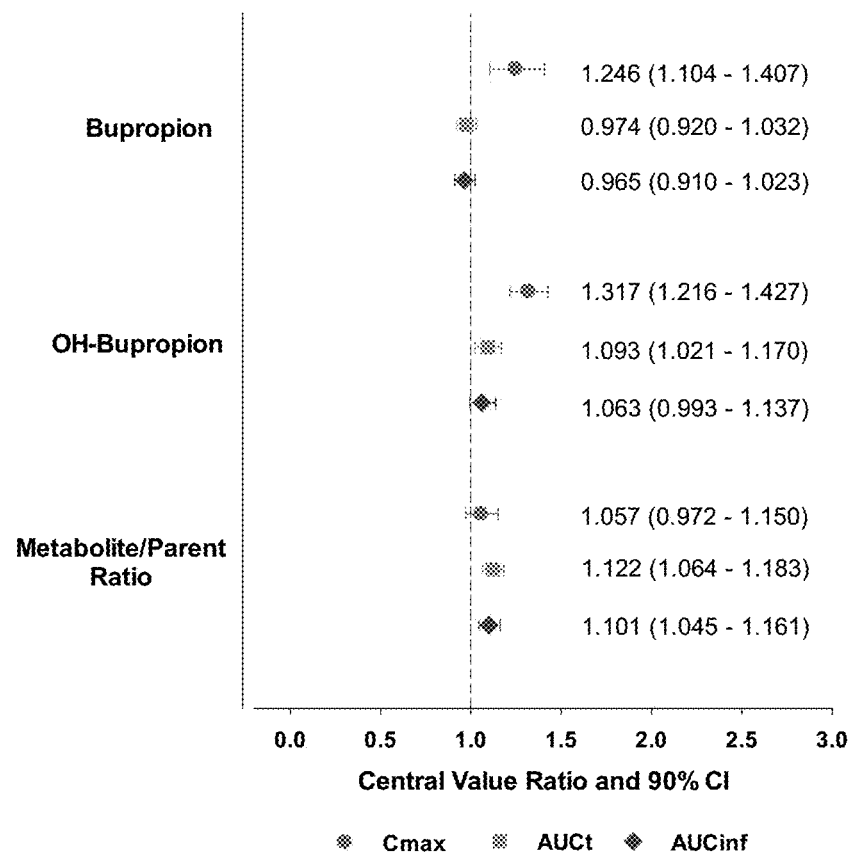
FIG. 3 shows results for elagolix sodium effects on metabolite/parent ratio PK.

Elagolix 300 mg BID dosing did not affect bupropion and OH-bupropion overall exposures (AUC values). Bupropion and OH-Bupropion $C_{max}$ values increased by 25% and 32%, respectively, upon co-administration with elagolix 300 mg BID (FIG. 3). Minimal changes (≤120%) were observed in the OH-bupropion/bupropion ratios of $C_{max}$ and AUC upon co-administration with elagolix 300 mg BID (FIG. 3).

There was no pattern to the adverse events reported, and no new safety issues were identified from this study. All treatment-emergent adverse events were mild in severity. No serious AEs were reported. No clinically significant abnormalities in vital signs, ECGs, physical examinations or laboratory measurements were observed during the course of the study.

Conclusion: Elagolix did not affect the bupropion PK at a clinically significant level; hence, no dose adjustment is required for bupropion (or any CYP21B6 substrate) when co-administered with elagolix. No dose adjustment for drugs that are metabolized by CYP21B6 is needed when co-administered with elagolix (300 mg BID for 10 days), as it did not induce CYP21B6 in this healthy volunteer study as opposed to in vitro findings. Co-administration of elagolix and bupropion was generally well tolerated by all subjects in the study; no new or unexpected safety findings were observed.

Example 2: Co-Administration with a CYP2C19 Substrate

A drug-drug interaction (DDI) study assessed the impact of elagolix sodium on the pharmacokinetics (PK) of a CYP2C19 substrate (omeprazole) in healthy premenopausal female volunteers. In particular, the objective of this study was to evaluate the effect of multiple doses of elagolix sodium on the pharmacokinetics of omeprazole and its metabolites using a single-arm study design in adult healthy premenopausal female subjects.

Subjects: Twenty adult premenopausal female subjects were enrolled in the study. All subjects completed the study and were included in the analyses (Table 3).

TABLE 3

Summary of Baseline Demographics for All Subjects

|  | Mean ± SD (N = 20) | Min-Max |
|---|---|---|
| Age (years) | 37.9 ± 6.69 | 26-48 |
| Weight (kg) | 72.4 ± 12.3 | 42.4-94.9 |
| Height (cm) | 163 ± 7.43 | 143-178 |
| BMI (kg/m$^2$) | 27.2 ± 3.28 | 20.1-29.9 |
| Race | 8 White (40%), 8 Black (40%), 4 Multiple-race (20%) | |

Methods: This was a single-center, multiple-dose, open-label, single-arm study designed to assess the effect of elagolix on the pharmacokinetics of omeprazole and its metabolites (5-hydroxyomeprazole and omeprazole sulfone) in healthy premenopausal female subjects between 18 and 49 years of age, inclusive.

Subjects received a single oral dose of omeprazole 40 mg that was administered under fasting conditions on Day 1. Beginning on Day 3, subjects received elagolix 300 mg BID under fasting conditions every day until Day 10. On Day 11, subjects received elagolix 300 mg BID and a single dose of omeprazole 40 mg under fasting conditions. Doses of elagolix were separated by approximately 12 hours.

Blood samples for omeprazole, 5-hydroxyomeprazole and omeprazole sulfone assays were collected prior to dosing (0 hour) and at 0.5, 1, 2, 3, 4, 6, 8, 10, 12 and 24 hours after dosing on Days 1 and 11. Plasma concentrations of omeprazole, 5-hydroxyomeprazole and omeprazole sulfone were determined using a validated liquid chromatography method with tandem mass spectrometric detection.

Pharmacokinetic parameters for omeprazole, 5-hydroxyomeprazole and omeprazole sulfone were estimated including $C_{max}$, $T_{max}$, $AUC_t$ and $AUC_{inf}$, as well as $t_{1/2}$. Additionally, the metabolite-to-parent (M:P) AUC ratios were calculated for both metabolites compared to omeprazole.

Testing was performed for CYP2C19 variants including the *2 (rs4244285), *3 (rs4986893), *4 (rs28399504), *8 (rs41291556), *10 (rs6413438) and *12 (rs55640102) alleles. The results of the CYP2C19 genetic polymorphism testing were used to evaluate the impact of CYP2C19 polymorphism on the pharmacokinetics of omeprazole and its metabolites. In addition, the magnitude of elagolix-omeprazole DDI was compared between the different subject subgroups based on CYP2C19 metabolizer status.

Safety was evaluated during confinement and at each study visit through adverse event monitoring, vital signs measurements, physical examinations, and routine laboratory tests.

Figure 4:
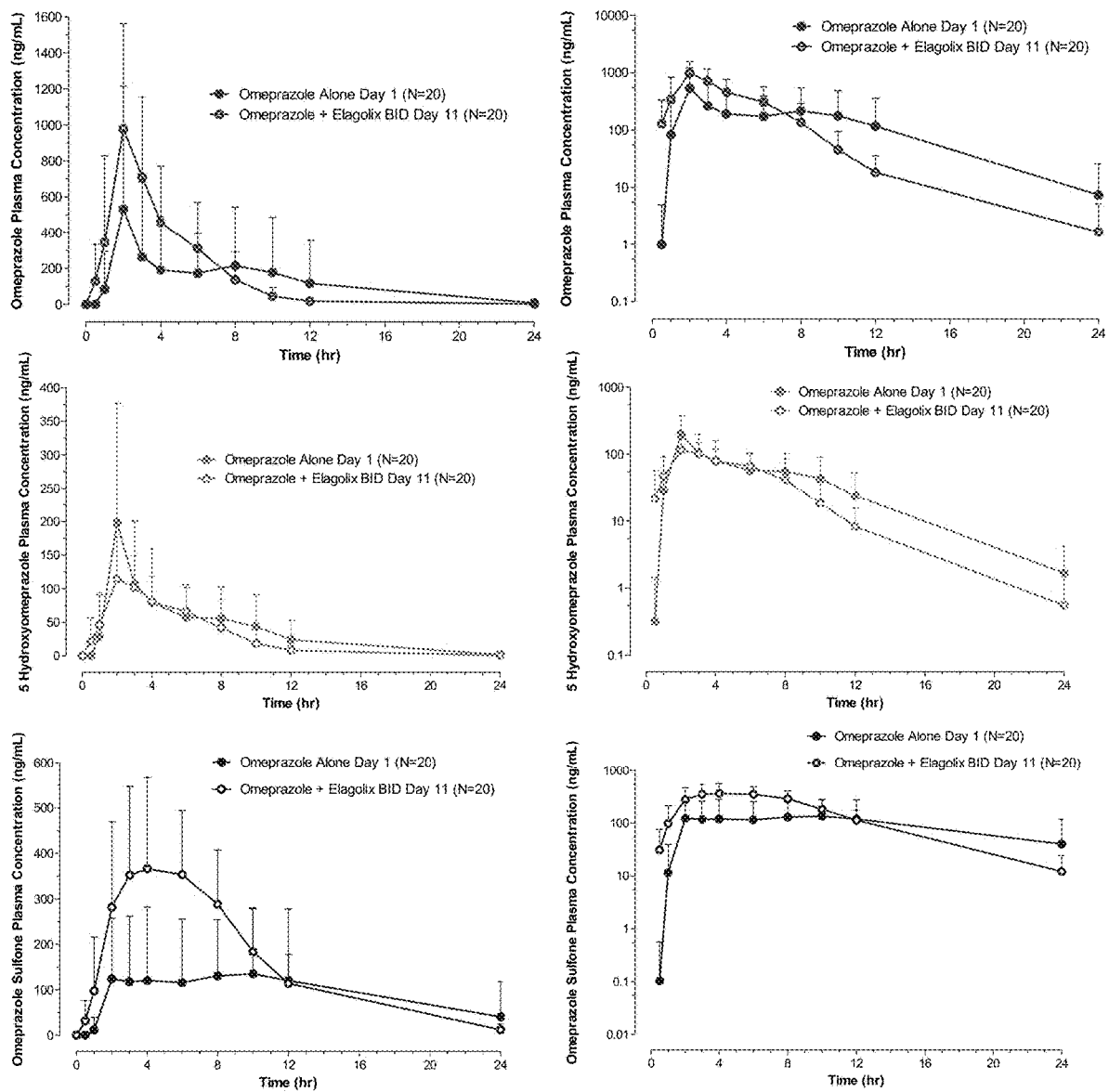
FIG. 4 shows mean (SD) plasma concentration-time profiles for omeprazole and its metabolites with/without elagolix sodium co-administration.
Figure 5:
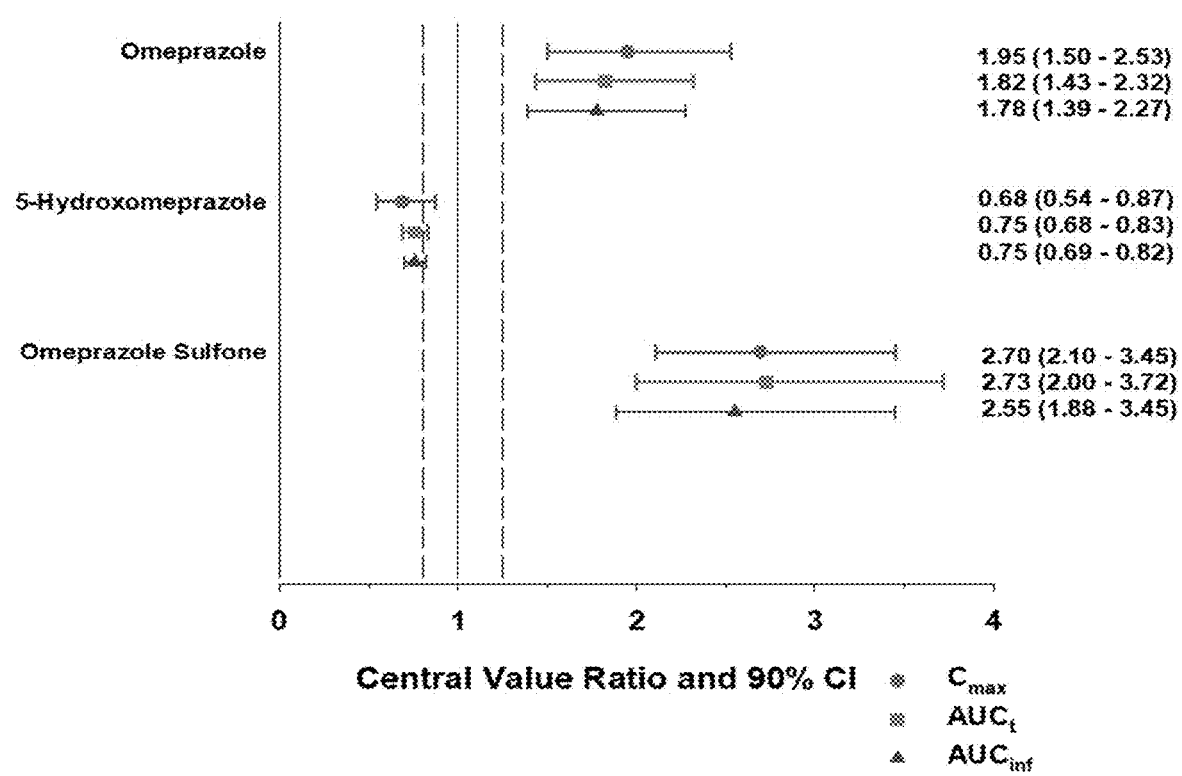
FIG. 5 shows point estimates and 90% confidence intervals for $C_{max}$ and AUC ratios of omeprazole, 5-hydroxyomeprazole, and omeprazole sulfone on Day 11 compared to Day 1.

Results: Mean (SD) concentration-time profiles and pharmacokinetic parameters of omeprazole and its metabolites when omeprazole is administered alone and in presence of elagolix are shown in FIG. 4 and Table 4, respectively.

TABLE 4

Geometric Mean (Mean, % CV) Pharmacokinetic Parameters of Omeprazole and its Metabolites.

| Pharmaco-kinetic Parameters | (Units) | Study Day 1 Omeprazole 40 mg (N = 20) | Study Day 11 Omeprazole 40 mg + Elagolix 300 mg BID (N = 20) |
|---|---|---|---|
| Omeprazole | | | |
| $C_{max}$ | (ng/mL) | 491 (717,88) | 956 (1130,47) |
| $T_{max}{}^a$ | (h) | 2.0 (2.0-10) | 2.0 (1.0-8.0) |
| $AUC_t$ | (ng·h/mL) | 1820 (3070,113) | 3320 (3760,44) |
| $AUC_{Inf}$ | (ng·h/mL) | 1880 (3200,113)$^c$ | 3360 (3790,44) |
| $t_{1/2}{}^b$ | (h) | 1.57 (0.773) | 1.65 (0.939) |
| 5-Hydroxyomeprazole | | | |
| $C_{max}$ | (ng/mL) | 491 (717,88) | 956 (1130,47) |
| $T_{max}{}^a$ | (h) | 2.0 (2.0-10) | 2.0 (1.0-8.0) |
| $AUC_t$ | (ng·h/mL) | 1820 (3070,113) | 3320 (3760,44) |
| $AUC_{inf}$ | (nghimL) | 1880 (3200,113)$^c$ | 3360 (3790,44) |
| $t_{1/2}{}^b$ | (h) | 1.57 (0.773)$^c$ | 1.65 (0.939) |
| $RAUC_t{}^a$ | | 0.65 (0.044-2.1) | 0.20 (0.071-0.84) |
| $RAUC_{inf}{}^a$ | | 0.61 (0.048-2.3)$^c$ | 0.20 (0.071-0.90) |
| Omeprazole Sulfone | | | |
| $C_{max}$ | (ng/mL) | 162 (219,78) | 411 (458,31) |
| $T_{max}{}^a$ | (h) | 3.5 (2.0-12) | 4.0 (3.0-8.0) |
| $AUC_t$ | (ng·h/mL) | 1240 (2250,104) | 3380 (3780,37) |
| $AUC_{inf}$ | (ng·h/mL) | 1400 (2100,107)$^c$ | 3450 (3860,38) |
| $t_{1/2}{}^b$ | (h) | 3.27 (1.59)$^d$ | 3.30 (0.821) |

TABLE 4-continued

Geometric Mean (Mean, % CV) Pharmacokinetic Parameters of Omeprazole and its Metabolites.

| Pharmaco-kinetic Parameters | (Units) | Study Day 1 Omeprazole 40 mg (N = 20) | Study Day 11 Omeprazole 40 mg + Elagolix 300 mg BID (N = 20) |
|---|---|---|---|
| $RAUC_t^a$ | | 0.76 (0.13-1.1) | 0.97 (0.67-1.6) |
| $RAUC_{inf}^a$ | | 0.85 (0.52-1.1)$^e$ | 0.99 (0.71-1.6) |

For the M:P AUC ratios, the central value ratios as well as the point estimates and 90% confidence intervals for the Day 11 versus Day 1 comparison are presented in Table 5.

TABLE 5

Comparison of Metabolite-to-Parent AUC Ratios for Omeprazole and its Metabolites with/without Elagolix Co-administration.

| Regimens Test vs. Reference | Pharmacokinetic Parameter | Central Value Test | Central Value Reference | Relative Bioavailability Point Estimate | 90% Confidences Interval |
|---|---|---|---|---|---|
| *5 Hydroxomeprazole: Omeprazole* | | | | | |
| Day 11 vs. Day 1 | M:P $AUC_t$ Ratio | 0.194 | 0.471 | 0.412 | 0.326, 0.520 |
| | M:P $AUC_{inf}$ Ratio | 0.198 | 0.458 | 0.432 | 0.343, 0.544 |
| *Omeprazole Sufone: Omeprazole* | | | | | |
| Day 11 vs. Day 1 | M:P $AUC_t$ Ratio | 1.017 | 0.679 | 1.497 | 1.272, 1.761 |
| | M:P $AUC_{inf}$ Ratio | 1.028 | 0.825 | 1.246 | 1.092, 1.422 |

Study Day 1: Omeprazole 40 mg (reference)
Study Day 11: Elagolix 300 mg BID+Omeprazole 40 mg (test)

Elagolix 300 mg BID dosing increased omeprazole $C_{max}$ by 1.9-fold and $AUC_{inf}$ 1.8-fold. 5-hydroxyomeprazole $C_{max}$ and $AUC_{inf}$ were decreased by approximately 30% and 25%, respectively. Elagolix 300 mg BID also increased omeprazole sulfone $C_{max}$ by 2.7-fold and $AUC_{inf}$ by 2.5-fold.

Elagolix 300 mg BID dosing decreased the M:P $AUC_{inf}$ ratio for 5-hydroxyomeprazole by 60% and increase the M:P $AUC_{inf}$ ratio for omeprazole sulfone by only 25%.

Figure 6:
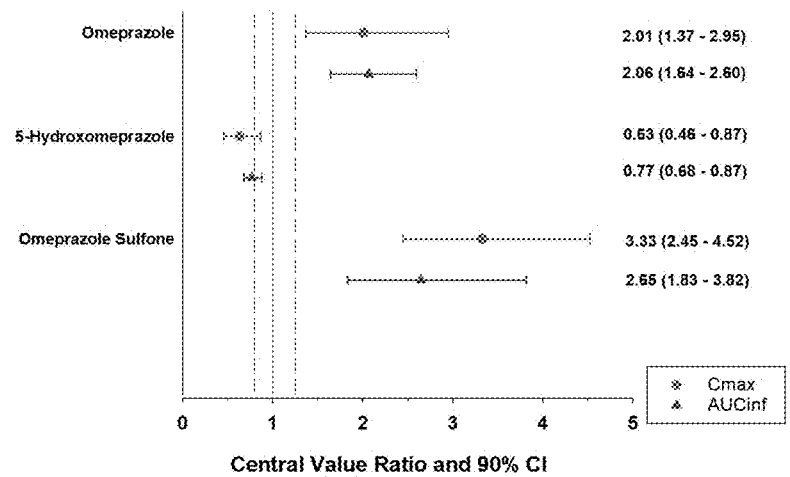
FIG. 6 shows point estimates and 90% confidence intervals for $C_{max}$ and AUC ratios of omeprazole, 5-hydroxyomeprazole, and omeprazole sulfone on Day 11 compared to Day 1 by CYP2C19 genotype.
Figure 6:
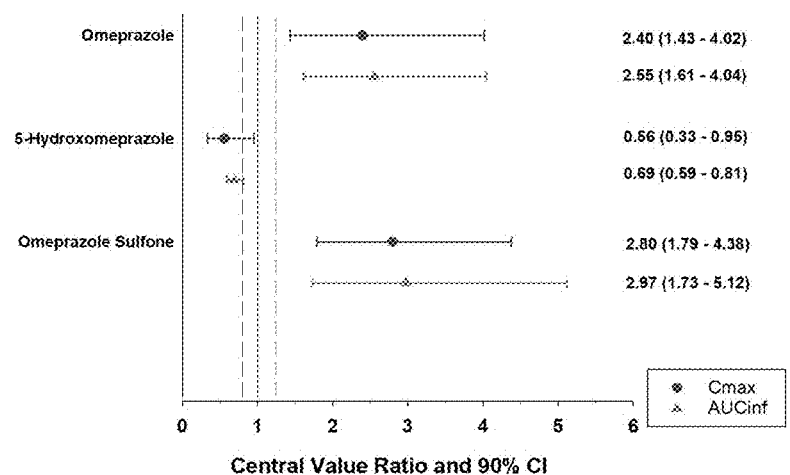
Figure 6:
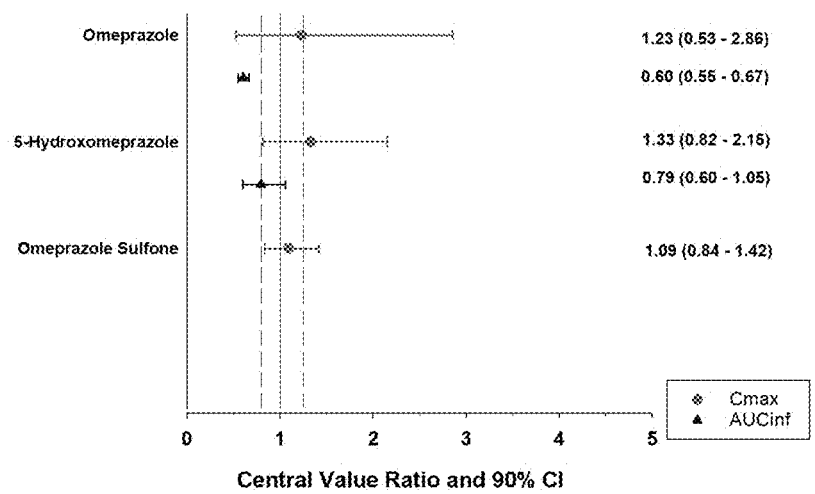

Twelve subjects were extensive metabolizers (EM) for CYP2C19, 5 were intermediate metabolizers (IM), and 3 were poor metabolizers (PM). The impact of elagolix co-administration on the pharmacokinetics of omeprazole and its metabolites is shown in FIG. 6 for each CYP2C19 genotype. Elagolix increased omeprazole exposures ($AUC_{inf}$) by 2- to 2.5-fold in EM and IM subjects, but decreased omeprazole $AUC_{inf}$ by 40% in PMs. 5-hydroxyomeprazole $AUC_{inf}$ decreased by 20-30% in all genotype subgroups, and omeprazole sulfone exposures increased by ~3-fold in EM and IM subjects.

The regimens tested were generally well tolerated by the subjects in this study.

Dose adjustments for concomitant therapy for a co-morbid condition for a given patient will depend on whether the patient is an extensive, intermediate or a poor metabolizer of CYP2C19. If the patient falls within a subpopulation of extensive metabolizers, greater dose adjustment would be required, and at the opposite end, if the patient falls within a subpopulation poor metabolizers, reduced or no dose adjustment would be required. The objective of such dose adjustments would be to bring the AUC and $C_{max}$ of the elagolix and the CYP2C19 substrate (e.g. omeprazole) that is concomitantly administered to a patient (having a co-morbid condition who requires both), to be substantially similar to the observed AUC and $C_{max}$, of the respective drugs, if the drug-drug interaction did not occur.

Example 3

Drug Interactions
Potential for ORIAHNN to Affect Other Drugs
ORIAHNN is a combination of elagolix, a gonadotropin-releasing hormone (GnRH) receptor antagonist, estradiol, an estrogen, and norethindrone acetate, a progestin, indicated for the management of heavy menstrual bleeding associated with uterine leiomyomas (fibroids) in premenopausal women.

Dosage and Administration
ORIAHNN is dosed and administered as one capsule (elagolix 300 mg, estradiol 1 mg, norethindrone acetate 0.5 mg) in the morning and one capsule (elagolix 300 mg) in the evening for up to 24 months.

Dosage Forms and Strengths
ORIAHNN is presented as a Morning (AM) capsule having elagolix 300 mg, estradiol 1 mg, norethindrone acetate 0.5 mg and an Evening (PM) capsule having elagolix 300 mg. (3) Elagolix is a weak to moderate inducer of cytochrome P450 (CYP3A). Co-administration with ORIAHNN may decrease plasma concentrations of drugs that are substrates of CYP3A.

Elagolix is a weak inhibitor of CYP2C19. Co-administration with ORIAHNN may increase plasma concentrations of drugs that are substrates of CYP2C19 (e.g., omeprazole and esomeprazole) (see Table 6).

Elagolix is an inhibitor of efflux transporter P-glycoprotein (P-gp). Co-administration with ORIAHNN may increase plasma concentrations of drugs that are substrates of P-gp (e.g., digoxin) (see Table 6).

The effect of co-administration of ORIAHNN on concentrations of concomitant drugs and the clinical recommendations for these drug interactions are summarized in Table 6.

TABLE 6

Drug Interactions: Effects of ORIAHNN on Other Drugs

| Concomitant Drug Class: Drug Name | Effect on Plasma Exposure of Concomitant Drug | Clinical Recommendations |
|---|---|---|
| Cardiac glycosides: digoxin | ↑ digoxin | Increase monitoring of digoxin concentrations and potential signs and symptoms of clinical toxicity when initiating or discontinuing ORIAHNN in patients who are taking digoxin. |
| Benzodiazepines: oral midazolam | ↓ midazolam | Consider increasing the dose of midazolam by no more than 2 fold and individualize midazolam therapy based on the patient's response. |
| Statins: rosuvastatin | ↓ rosuvastatin | Monitor lipid levels and adjust the dose of rosuvastatin, if necessary. |
| Proton pump inhibitors: omeprazole | ↑ omeprazole | No dose adjustment needed for omeprazole 40 mg once daily when co-administered with ORIAHNN. When ORIAHNN is used concomitantly with higher doses of omeprazole, consider dosage reduction of omeprazole. |

The direction of the arrow indicates the direction of the change in the area under the curve (AUC) (↑ = increase, ↓ = decrease).

Potential for Other Drugs to Affect ORIAHNN

Elagolix is a substrate of CYP3A, P-gp, and OATP1B1; estradiol and norethindrone acetate are metabolized partially by CYP3A.

Concomitant use of ORIAHNN and strong CYP3A inducers may decrease elagolix, estradiol and norethindrone plasma concentrations and may result in a decrease in the therapeutic effects of ORIAHNN.

The concomitant use of rifampin increased plasma concentrations of elagolix. Concomitant use of ORIAHNN and rifampin is not recommended.

Concomitant use of ORIAHNN and strong CYP3A inhibitors (e.g., ketoconazole, grapefruit juice) is not recommended. Concomitant use of ORIAHNN with strong CYP3A inhibitors may increase elagolix, estradiol and norethindrone plasma concentrations and increase the risk of adverse reactions.

Co-administration of ORIAHNN with drugs that inhibit OATP1B1 may increase elagolix plasma concentrations. Concomitant use of ORIAHNN and strong OATP1B1 inhibitors (e.g., cyclosporine) is contraindicated.

Example 4

Use of ORIAHNN in Specific Populations

Pregnancy

Risk Summary

Use of ORIAHNN is contraindicated in pregnant women. Exposure to elagolix early in pregnancy may increase the risk of early pregnancy loss. Discontinue ORIAHNN if pregnancy occurs during treatment.

The limited human data with the use of elagolix in pregnant women are insufficient to determine whether there is a risk for major birth defects or miscarriage.

When pregnant rats and rabbits were orally dosed with elagolix during the period of organogenesis, postimplantation loss was observed in pregnant rats at doses 12 times the maximum recommended human dose (MRHD). Spontaneous abortion and total litter loss were observed in rabbits at doses 4 and 7 times the MRHD. There were no structural abnormalities in the fetuses at exposures up to 25 and 7 times the MRHD for the rat and rabbit, respectively.

Data

Human Data

There was one pregnancy reported out of the 453 women who received ORIAHNN in the Phase 3 uterine fibroids clinical trials. The pregnancy resulted in a spontaneous abortion and the estimated fetal exposure to ORIAHNN occurred during the first 18 days of pregnancy.

Animal Data

Embryofetal development studies were conducted in the rat and rabbit. Elagolix was administered by oral gavage to pregnant rats (25 animals/dose) at doses of 0, 300, 600 and 1200 mg/kg/day and to rabbits (20 animals/dose) at doses of 0, 100, 150, and 200 mg/kg/day, during the period of organogenesis (gestation day 6-17 in the rat and gestation day 7-20 in the rabbit).

In rats, maternal toxicity was present at all doses and included six deaths and decreases in body weight gain and food consumption. Increased post implantation losses were present in the mid dose group, which was 12 times the MRHD based on AUC. In rabbits, three spontaneous abortions and a single total litter loss were observed at the highest, maternally toxic dose, which was 7 times the MRHD based on AUC. A single total litter loss occurred at a lower non-maternally toxic dose of 150 mg/kg/day, which was 4 times the MRHD.

No fetal malformations were present at any dose level tested in either species even in the presence of maternal toxicity. At the highest doses tested, the exposure margins were 25 and 7 times the MRHD for the rat and rabbit, respectively. However, because elagolix binds poorly to the rat gonadotropin-releasing hormone (GnRH) receptor (~1000 fold less than to the human GnRH receptor), the rat study is unlikely to identify pharmacologically mediated effects of elagolix on embryofetal development. The rat study is still expected to provide information on potential non-target-related effects of elagolix.

In a pre- and postnatal development study in rats, elagolix was given in the diet to achieve doses of 0, 100 and 300 mg/kg/day (25 per dose group) from gestation day 6 to lactation day 20. There was no evidence of maternal toxicity. At the highest dose, two dams had total litter loss, and two failed to deliver. Pup survival was decreased from birth to postnatal day 4. Pups had lower birth weights and lower body weight gains were observed throughout the pre-weaning period at 300 mg/kg/day. Smaller body size and effect on startle response were associated with lower pup weights at 300 mg/kg/day. Post-weaning growth, development and behavioral endpoints were unaffected.

Maternal plasma concentrations in rats on lactation day 21 at 100 and 300 mg/kg/day (47 and 125 ng/mL) were 0.04-fold and 0.1-fold the maximal elagolix concentration ($C_{max}$) in humans at the MRHD. Because the exposures achieved in rats were much lower than the human MRHD, this study is not predictive of potentially higher lactational exposure in humans.

Lactation

Risk Summary

ORIAHNN is not recommended during lactation. There is limited information on the presence of elagolix in human milk, the effects on the breastfed child, or the effects on milk production.

Data

There is no information on the presence of elagolix or its metabolites in human milk, the effects on the breastfed child, or the effects on milk production. Estrogen administration to nursing women has been shown to decrease the quantity and quality of the breast milk. Detectable amounts of estrogen and progestin have been identified in the breast milk of women receiving estrogen and progestin combinations.

There are no adequate animal data on excretion of elagolix in milk.

Females and Males of Reproductive Potential

Based on the mechanism of action of elagolix, there is a risk of early pregnancy loss if ORIAHNN is administered to a pregnant woman.

Pregnancy Testing

ORIAHNN may delay the ability to recognize the occurrence of a pregnancy because it may reduce the intensity, duration and amount of menstrual bleeding. Exclude pregnancy before initiating treatment with ORIAHNN. Perform pregnancy testing if pregnancy is suspected during treatment with ORIAHNN and discontinue treatment if pregnancy is confirmed.

Renal Impairment

No dose adjustment of ORIAHNN is required in women with any degree of renal impairment or end-stage renal disease (including women on dialysis).

Hepatic Impairment

ORIAHNN is contraindicated in women with any liver impairment or disease.

Example 5

Drug Interaction Studies

Drug interaction studies were performed with elagolix and other drugs likely to be co-administered and with drugs commonly used as probes for pharmacokinetic interactions. Tables 7 and 8 summarize the pharmacokinetic effects when elagolix was co-administered with these drugs.

TABLE 7

Drug Interactions: Change in Pharmacokinetics of Elagolix in the Presence of Co-administered Drugs

| Co-administered Drug | Co-administered Drug Regimen | Elagolix Regimen | N | Ratio (90% CI)* $C_{max}$ | AUC |
|---|---|---|---|---|---|
| Ketoconazole | 400 mg once daily | 150 mg single dose& | 11 | 1.77 (1.48-2.12) | 2.20 (1.98-2.44) |
| Rifampin | 600 mg single dose | 150 mg single dose& | 12 | 4.37 (3.62-5.28) | 5.58 (4.88-6.37) |
| | 600 mg once daily | | | 2.00 (1.66-2.41) | 1.65 (1.45-1.89) |

CI: Confidence interval
&The elagolix dose in these studies was 0.5 times the approved dose in ORIAHNN (0.25 times the total approved daily dosage of elagolix in ORIAHNN)
*ratios for $C_{max}$ and AUC compare co-administration of the medication with elagolix vs. administration of elagolix alone.

No clinically significant changes in elagolix exposures were observed when elagolix 300 mg twice daily was co-administered with rosuvastatin (20 mg once daily), sertraline (25 mg once daily) or fluconazole (200 mg single dose). The effect of co-administered rosuvastatin, sertraline or fluconazole on E2/NETA has not been studied.

TABLE 8

Drug Interactions: Change in Pharmacokinetics of Co-administered Drug in the Presence of Elagolix

| Co-administered Drug | Co-administered Drug Regimen | Elagolix Regimen | N | Ratio (90% CI)* $C_{max}$ | AUC |
|---|---|---|---|---|---|
| Digoxin | 0.5 mg single dose | 200 mg twice daily ×10 days | 11 | 1.71 (1.53-1.91) | 1.26 (1.17-1.35) |
| Rosuvastatin | 20 mg once daily | 300 mg twice daily ×7 days | 10 | 0.99 (0.73-1.35) | 0.60 (0.50-0.71) |
| Midazolam | 2 mg single dose | 300 mg twice daily ×11 days | 20 | 0.56 (0.51-0.62) | 0.46 (0.41-0.50) |

TABLE 8-continued

Drug Interactions: Change in Pharmacokinetics of
Co-administered Drug in the Presence of Elagolix

| Co-administered Drug | Co-administered Drug Regimen | Elagolix Regimen | N | Ratio (90% CI)* | |
|---|---|---|---|---|---|
| | | | | $C_{max}$ | AUC |
| | 2 mg single dose | 150 mg once daily ×13 days | 11 | 0.81 (0.74-0.89) | 0.65 (0.58-0.72) |
| Omeprazole | 40 mg single dose | 300 mg twice daily ×9 days | 20 | 1.95 (1.50-2.53) | 1.78 (1.39-2.27) |

CI: Confidence interval
*ratios for $C_{max}$ and AUC compare co-administration of the medication with elagolix vs. administration of the medication alone.

No clinically significant changes in sertraline, fluconazole, bupropion, or transdermal patch E2/NETA 0.51/4.8 mg exposures were observed when co-administered with elagolix 300 mg twice daily Pharmacogenomics Hepatic uptake of elagolix involves the OATP1B1 transporter protein. Higher plasma concentrations of elagolix have been observed in patients who have two reduced function alleles of the gene that encodes OATP1B1 (SLCO1B1 521T>C) (these patients are likely to have reduced hepatic uptake of elagolix; and thus, higher plasma elagolix concentrations). The frequency of this SLCO1B1 521 C/C genotype is generally less than 500 in most racial/ethnic groups. Women with this genotype are expected to have approximately 2-fold higher elagolix mean concentrations compared to women with normal transporter function (i.e., SLCO1B1 521T/T genotype). Adverse effects of elagolix have not been fully evaluated in subjects who have two reduced function alleles of the gene that encodes OATP1B1 (SLCO1B1 521T>C). The above listed examples should not be deemed to limit the scope of the invention as claimed.

The invention claimed is:

1. A method for management of heavy menstrual bleeding associated with uterine leiomyomas (fibroids) or management of moderate to severe pain associated with endometriosis, the method comprising: orally administering to a patient in need thereof elagolix sodium, wherein the patient concomitantly receives omeprazole, wherein the omeprazole is administered without an adjustment to a recommended omeprazole dosing schedule and the recommended omeprazole dosing schedule comprises a 40 mg dose administered once per day.

2. A method for management of heavy menstrual bleeding associated with uterine leiomyomas (fibroids) or management of moderate to severe pain associated with endometriosis, the method comprising: orally administering to a patient in need thereof elagolix sodium, wherein the patient concomitantly receives omeprazole, wherein the omeprazole is administered according to a modified omeprazole dosing schedule, such modified omeprazole dosing schedule comprising a reduced omeprazole dose and/or a reduced frequency of omeprazole administration relative to a recommended omeprazole dosing schedule.

3. The method of claim 2, wherein the recommended omeprazole dosing schedule comprises (i) a 60 mg dose administered once per day and/or (ii) a 120 mg dose administered three times per day.

4. The method of claim 2, wherein the modified omeprazole dosing schedule provides (i) an omeprazole $AUC_{inf}$ ratio comparing (A) omeprazole $AUC_{inf}$ when co-administered with elagolix to (B) omeprazole $AUC_{inf}$ when administered alone between about 0.5 and about 2.0 and/or (ii) an omeprazole $C_{max}$ ratio comparing (A) omeprazole $C_{max}$ when co-administered with elagolix to (B) omeprazole $C_{max}$ when administered alone between about 0.5 and about 2.0.

5. The method of claim 4 wherein the method is for the management of moderate to severe pain associated with endometriosis.

6. The method of claim 5, wherein elagolix sodium is administered in an amount equivalent to 150 mg of elagolix free acid once daily or elagolix sodium is administered in an amount equivalent to 200 mg of elagolix free acid twice daily.

7. The method of claim 1, wherein the method is for the management of heavy menstrual bleeding associated with uterine leiomyomas (fibroids).

8. The method of claim 7, wherein elagolix sodium is administered in an amount equivalent to 300 mg of elagolix free acid twice daily.

9. The method of claim 8, wherein elagolix sodium is administered with an estrogen and progestin combination.

10. The method of claim 9, wherein the estrogen and progestin combination comprises estradiol and norethindrone acetate.

11. A method for management of heavy menstrual bleeding associated with uterine leiomyomas (fibroids), the method comprising: orally administering to a patient in need thereof elagolix sodium, wherein elagolix sodium is administered in an amount equivalent to 300 mg of elagolix free acid twice daily; wherein the patient receives a dose of 40 mg of omeprazole; and wherein: (i) an omeprazole $C_{max}$ ratio, which compares (A) omeprazole $C_{max}$ when co-administered in the presence of elagolix to (B) omeprazole $C_{max}$ when administered alone, is 1.95 with a 90% confidence interval of 1.50-2.53; and/or (ii) an omeprazole $AUC_{inf}$ ratio, which compares (A) omeprazole $AUC_{inf}$ when co-administered in the presence of elagolix to (B) omeprazole $AUC_{inf}$ when administered alone, is 1.78 with a 90% confidence interval of 1.39-2.27.

12. The method of claim 11, wherein elagolix sodium is administered with an estrogen and progestin combination.

13. The method of claim 12, wherein the estrogen and progestin combination comprises estradiol and norethindrone acetate.

14. A method for management of heavy menstrual bleeding associated with uterine leiomyomas (fibroids), the method comprising: orally administering to a patient in need thereof elagolix sodium, wherein elagolix sodium is administered in an amount equivalent to 300 mg of elagolix free acid twice daily; further wherein elagolix sodium is used concomitantly with omeprazole and a recommended omeprazole dosage amount is 60 mg per day or more, said patient receives a reduced omeprazole dose and/or a reduced frequency of omeprazole dosing.

15. A method for management of heavy menstrual bleeding associated with uterine leiomyomas (fibroids), the method comprising: orally administering to a patient in need thereof elagolix sodium, wherein elagolix sodium is administered in an amount equivalent to 300 mg of elagolix free acid twice daily; further wherein said patient receives a drug that is metabolized by CYP2C19 pathway at a reduced daily dose, such that said drug is omeprazole, and the reduced daily dose of omeprazole is between 10 mg to less than 360 mg.

16. A method for management of heavy menstrual bleeding associated with uterine leiomyomas (fibroids), the method comprising: orally administering to a patient in need thereof elagoliX sodium, wherein elagoliX sodium is administered in an amount equivalent to 300 mg of elagoliX free acid twice daily; further wherein said patient receives a drug that is metabolized by CYP2C19 pathway at a reduced daily dose such that said drug is omeprazole, and the reduced daily dose of omeprazole is between 10 mg to less than 360 mg.

17. A method for management of moderate to severe pain associated with endometriosis, the method comprising: orally administering to a patient in need thereof elagoliX sodium, wherein elagoliX sodium is administered in an amount equivalent to 150 mg of elagoliX free acid once a day or 200 mg of elagolix free acid twice a day; further wherein said patient receives a drug that is metabolized by CYP2C19 pathway at a reduced daily dose, such that said drug is omeprazole, and the reduced daily dose of omeprazole is between 10 mg to less than 360 mg.

* * * * *

UNITED STATES PATENT AND TRADEMARK OFFICE
CERTIFICATE OF CORRECTION

| | |
|---|---|
| PATENT NO. | : 11,690,845 B2 |
| APPLICATION NO. | : 17/004817 |
| DATED | : July 4, 2023 |
| INVENTOR(S) | : Farah N. Ali et al. |

Page 1 of 1

It is certified that error appears in the above-identified patent and that said Letters Patent is hereby corrected as shown below:

In the Claims

Claim 15, Column 29, Line 5-14, "A method for management of heavy menstrual bleeding associated with uterine leiomyomas (fibroids), the method comprising: orally administering to a patient in need thereof elagolix sodium, wherein elagolix sodium is administered in an amount equivalent to 300 mg of elagolix free acid twice daily; further wherein said patient receives a drug that is metabolized by CYP2C19 pathway at a reduced daily dose such that said drug is omeprazole, and the reduced daily dose of omeprazole is between 10 mg to less than 360 mg." should be changed to --A method for management of moderate to severe pain associated with endometriosis, the method comprising: orally administering to a patient in need thereof elagolix sodium, wherein elagolix sodium is administered in an amount equivalent to 150 mg of elagolix free acid once a day or 200 mg of elagolix free acid twice a day; further wherein elagolix sodium is used concomitantly with omeprazole and a recommended omeprazole dosage amount is 60 mg per day or more, said patient receives a reduced omeprazole dose and/or a reduced frequency of omeprazole dosing.--.

Claim 16, Column 29, Line 18, "thereof elagoliX sodium, wherein elagoliX sodium" should be changed to --thereof elagolix sodium, wherein elagolix sodium--.

Claim 16, Column 30, Line 1, "300 mg of elagoliX" should be changed to --300 mg of elagolix--.

Claim 17, Column 30, Lines 9-11, "in need thereof elagoliX sodium, wherein elagoliX sodium is administered in an amount equivalent to 150 mg of elagoliX" should be changed to --in need thereof elagolix sodium, wherein elagolix sodium is administered in an amount equivalent to 150 mg of elagolix--.

Signed and Sealed this
Twenty-ninth Day of August, 2023

Katherine Kelly Vidal
*Director of the United States Patent and Trademark Office*